United States Patent [19]
Marburg et al.

[11] Patent Number: 5,371,197
[45] Date of Patent: Dec. 6, 1994

[54] PROTEIN-DIMERIC POLYSACCHARIDE CONJUGATE VACCINE

[75] Inventors: Stephen Marburg, Metuchen; Richard L. Tolman, Warren, both of N.J.

[73] Assignee: Merck & Co., Inc., Rahway, N.J.

[21] Appl. No.: 766,242

[22] Filed: Sep. 24, 1991

[51] Int. Cl.$^5$ .................. C07K 17/02; C07K 17/10; A61K 39/385; A61K 39/116

[52] U.S. Cl. .................. 530/404; 530/402; 530/403; 530/405; 530/408; 530/409; 530/395; 424/194.1; 424/197.11; 424/203.1; 424/244.1; 424/256.1; 424/831

[58] Field of Search ............. 530/402, 403, 395, 404, 530/405, 408, 409; 424/92; 536/55.1

[56] References Cited

U.S. PATENT DOCUMENTS

| | | | |
|---|---|---|---|
| 4,271,147 | 6/1981 | Helting et al. | |
| 4,619,828 | 10/1986 | Gordon | 424/92 |
| 4,686,102 | 8/1987 | Ritchey et al. | 424/92 |
| 4,695,624 | 9/1987 | Marburg et al. | 530/395 |
| 4,711,779 | 12/1987 | Porro | 424/92 |
| 4,830,852 | 5/1989 | Marburg | 424/85.8 |
| 4,882,317 | 11/1989 | Marburg | 514/54 |
| 5,034,519 | 7/1991 | Beuvery et al. | 536/117 |

FOREIGN PATENT DOCUMENTS

| | | |
|---|---|---|
| 0161188 | 5/1984 | European Pat. Off. |
| 0186576 | 12/1984 | European Pat. Off. |
| 0208375A2 | 7/1985 | European Pat. Off. |

OTHER PUBLICATIONS

Lerner, R. A. et al. (1983) in: The Biology of Immunologic Disease, F. J. Dixon & D. W. Fisher, eds., HP Publishing Co. Inc., New York, NY, pp. 331-338.
Evenberg, et al. *J. of Infect. Diseases*, 165: No. S1, pp. S152-S155 (1992).
Lang, et al., *Dev. Biol. Standard*, 71: pp. 121-126 (1990).
McQueen, et al., Pediatrics Res.: Meeting held in Apr.-May, 1991, 29: No. 4PT2, pp. 179A, (1991).
S. Marburg et al., Bimolecular Chemistry of Macromolecules: Synthesis of Bacterial Polysaccharide Conjugates with *Neisseria meningitis* Membrane Protein, *J. Am. Chem. Soc.*, vol. 108, pp. 5282-5287 (1986).
Frasch et al (1988) J. Infectious Dis. 158(4):710-718.
Lifely et al (1991) Vaccine 9:60-66.

*Primary Examiner*—Kay K. A. Kim
*Attorney, Agent, or Firm*—Hesna J. Pfeiffer; Richard J. Parr; Gerard H. Bencen

[57] ABSTRACT

A conjugate immunogen, having polysaccharide moieties derived from bacterial sources, provides a multivalent vaccine with a low protein to polysaccharide ratio. The vaccine reduces complications associated with injection of protein immunogens due to pyrogenic responses, such as swelling and pain, and is particularly suitable for administration to infants.

7 Claims, No Drawings

PROTEIN-DIMERIC POLYSACCHARIDE CONJUGATE VACCINE

BACKGROUND OF THE INVENTION

Purified capsular polysaccharides of bacteria have been used to prepare vaccines against the cognate bacteria. Resulting immune responses have often been less satisfactory than desirable, particularly in very young children or individuals with immature or deficient immunological systems. The *Haemophilus influenzae* type b capsular polysaccharide by itself, for example, fails to provide an adequate immune response in infants. Thus this polysaccharide is ineffective in providing protection against the serious pediatric medical problems caused by *H. influenza* type b bacterial infections.

Enhancement of the immunogenicity of polysaccharides may often be accomplished by combining them with proteins [Schneerson et al., "Haemophilus Influenzae Type b Polysaccharide-Protein Conjugates: Model for a New Generation of Capsular Polysaccharide Vaccines," *New Dev. With Hum. & Vet. Vaccines.*, 77–94 (1980); Schneerson, et al., *J. Exptl. Med.*, 152:361 (1980); Anderson, *Infection and Immunity*, 39:233 (1983)].

Care must be exercised in the selection of the protein which is to be combined with these polysaccharides, however, as certain proteins (e.g. pertussinogen) are non-specific stimulators of the immune system in infants. These proteins can, to a degree, enhance the immune response to polysaccharide antigens, but unfortunately such non-specific activation leads to unwanted biological effects such as reactogenicity. The much preferred specific enhanced immune response to these polysaccharides can be achieved in infants by "conjugating" these polysaccharides to appropriate proteins, as first reported by Goebel et al., [*J. Exptl. Med.* 50:521–531 (1929)].

The means of combining the polysaccharide and protein must also be carefully considered. If, as is believed, the immunological enhancement is realized as a result of the molecular proximity of the polysaccharide determinants to the protein "carrier" determinants, these moieties should not easily separate in the biological system. Non-covalent complexes, arising from the polyanionic character of the polysaccharides and the polycationic character of "carrier" proteins, may stimulate immune responses, but these complexes are chemically labile and the resultant immune responses appear to show T-cell independency, and may be poorly reproducible. By contrast, covalent conjugates of polysaccharides and protein possess much greater chemical stability and may demonstrate T-cell dependent immune responses, and good reproducibility.

Covalent polysaccharide-protein conjugates have been disclosed in the literature, but the exact nature of the covalent linkage has not been proven or quantified since the only assay for covalency has been activity in vivo and the processes disclosed in the literature have been difficult to reproduce. *Haemophilus influenzae* type b or *Streptococcus pneumoniae* type 6A polysaccharides (PnPs6A) was reacted with cyanogen bromide, then with adipic acid dihydrazide, then "coupled" with tetanus toxoid or horseshoe crab hemocyanin proteins in Schneerson et al., (*J. Exptl. Med.* 1.52:361 (1980); *Infection and Immunity* 40:245 (1983)). Pneumococcal type 19 F polysaccharide (PnPs19 F) was coupled to bovine serum albumin directly by forming imines (Schiff bases) from the reducing ends of the polysaccharides and the pendant amine groups (i.e., lysines) of the protein, then reducing these imines with sodium cyanoborohydride [Lin et al. *Immunology* 46:333 (1982)].

Additionally, polysaccharides linked to diazotized aromatic amines were coupled to the protein's tyrosines in K. K. Nixdorff et al., [*Immunology* 29:87 (1975)]and polysaccharides linked to isothiocyanates, which were then linked to the pendant amino groups of the protein's lysine in Svenson et al., [*J. Immunolog. Methods* 25:323 (1979)]. In each case, however, the resulting conjugate was characterized only by its gel permeation chromatographic behavior. In still another example [Nutani et al., *Infection and Immunity* 36:971 (1982)]the polysaccharide, pullulan, was activated with cyanuric chloride, then reacted with tetanus toxoid. In this case, the conjugates were characterized by electrophoresis and only shown to be different from the starting materials.

Marburg et al., in U.S. Pat. No. 4,695,624, describe covalently-modified bacterial polysaccharides and chemically-stable conjugates of such polysaccharides with covalently-modified immunogenic membrane proteins, viral protein subunits, synthetic polypeptides, bacterial toxoids or other suitable immunogenic proteins, which conjugates are useful components of immunogenic anti-bacterial vaccines. The polysaccharide and protein entities are coupled through bigeneric spacers containing a covalent thioether group. These spacers are atom chains linking polysaccharide and protein macromolecules. One end of the spacer originates with a covalently modified polysaccharide, while the other end originates with the functionalized protein.

The instant invention differs from the invention disclosed in the U.S. Pat. No. 4,695,624 in that a conjugate vaccine is produced that has an increased polysaccharide to protein ratio and has the ability to induce immune responses protective against infection by more than one bacterial pathogen.

SUMMARY OF THE INVENTION

The invention is a polysaccharide-protein conjugate vaccine having a polysaccharide dimer or multimer linked to each reactive site on a carrier more than one molecule of molecule of protein. This allows for the generation of a multivalent vaccine having a low protein to polysaccharide ratio. This diminished ratio minimizes "protein load" problems such as pyrogenic response, swelling and pain which are often associated with injection of protein immunogens.

The vaccine comprises stable, covalently coupled, heterodimeric polysaccharide-protein conjugates of bacterial polysaccharides and immunogenic proteins coupled through bigeneric spacers according to the structure: $Ps_2$-$spacer_2$-$Ps_1$-$spacer_1$-PRO, wherein: $Ps_1$ and $Ps_2$ represent the same or different bacterial polysaccharides, but preferably different poysaccharides; $spacer_1$ represents an atomic chain linking the $Ps_1$ and protein moieties to form a $Ps_1$-$spacer_1$-PRO complex; $spacer_2$ represents an atomic chain linking the $Ps_1$-$spacer_1$-PRO complex to $Ps_2$; and PRO represents the protein moiety which acts as a carrier and confers enhanced immunogenicity polysaccharide moieties which are otherwise poorly immunogenic, especially in infants and immunocompromised individuals.

The instant invention differs from the invention disclosed in the U.S. Pat. Nos. 4,695,624 and 4,830,852 in that a conjugate vaccine is produced that has an increased polysaccharide to protein ratio. The invention is predicated on the fact that when $Ps_1$ is activated to display a pendant electrophile, such as a haloacetyl group, and when reacted with a protein activated to display a nucleophilic group, such as a sulfhydryl, many electrophilic groups are still displayed on $Ps_1$ subsequent to formation of the $Ps_1$-$spacer_1$-PRO conjugate. This invention takes advantage of these residual electrophilic groups by reacting $Ps_2$ activated to display pendant nucleophilic groups, such as a sulfhydryl, with the already formed $Ps_1$-$spacer_1$-PRO conjugate having residual electrophilic groups on $Ps_1$. This series of reactions may be summarized as follows for example using bromoacetyl groups (BrAc) as the electrophile, and sulfhydryls as the nucleophile, $Ps_1$-$(BrAc)_n$+PRO-$(SH)_m \rightarrow$ PRO-S-$Ps_1$-$(BrAc)_{n-m}$; PRO-S-$Ps_1$-$(BrAc)_{n-m}$+$Ps_2$-$(SH)_x \rightarrow$ PRO-S-$Ps_1$-S-$Ps_2$; wherein n, m, and x define the molar amounts of the indicated reactant, and n>m, x≧n-m, or, if x<n-m, then a capping step to remove residual reactive sites is required.

Likewise, when $Ps_1$ is activated to display pendant nucleophilic groups, such as sulfhydryl groups, PRO is activated to display pendant electrophilic groups. $Ps_2$ is activated to display pendant electrophilic groups allowing, $Ps_2$ to react with a pre-formed $Ps_1$-$spacer_1$-PRO conjugate having residual pendant nucleophilic groups on $Ps_1$. Thus, this series of reactions may be summarized as follows: $Ps_1$-$(SH)_n$+PRO-$(BrAc)_m \rightarrow$ PRO-S-$Ps_1$-$(SH)_{n-m}$; PRO-S-$Ps_1$-$(SH)_{n-m}$+$Ps_2$-$(BrAc)_x \rightarrow$ PRO-S-$Ps_1$-S-$Ps_2$; with n, m, and x as defined above.

Preferably, $Ps_1$ is a *Streptococcus pneumoniae* capsular polysaccharide (PnPs) or *Haemophilus influenzae* b capsular polysaccharide, and $Ps_2$ is *H. influenzae* b polysaccharide or a PnPs capsular polysaccharide, and PRO is an outer membrane protein of *Neisseria meningitidis* b. $Spacer_1$ and $spacer_2$ are preferably: —CONH(CH$_2$)$_5$CONH(CH$_2$)$_3$—O—(CH$_2$)$_4$—O—(CH$_2$)$_3$—NH-COCH$_2$CH—(COOH)—S—CH$_2$CONH(CH$_2$)$_4$CONH—, —CONH—(CH$_2$)$_3$—O—(CH$_2$)$_4$—O—(CH$_2$)$_3$NHCO(CH$_2$)$_5$NHCOCH$_2$CH—(COOH)—S—CH$_2$CONH(CH$_2$)$_4$CONH—, or a butane diaminyl-S-carboxymethyl-homocysteinyl complex.

The invention is also a method for making a heterodimeric polysaccharide-protein conjugate which comprises the steps of either:

(I)

a) forming a polysaccharide-protein conjugate having residual haloacetyl groups which are reactive toward sulfhydryl groups;

b) succinylating an amino derivatized second polysaccharide with S-acetylmercapto succinic anhydride and deacetylating with hydroxyl amine to form sulfhydryl groups such that this polysaccnaride will react with the polysaccharide-protein conjugate displaying residual haloacetyl groups;

c) displacing the halogen from one of the residual haloacetyl groups on the polysaccharide-protein conjugate with the liberated sulfhydryl on the second polysaccharide; or (II)

a) forming a polysaccharide-protein conjugate having residual sulfhydryl groups which are reactive toward a second haloacetylated polysaccharide;

b) haloacetylating a second polysaccharide such that this polysaccharide will react with the polysaccharide-protein conjugate displaying residual sulfhydryl groups;

c) displacing the halogen from the haloacetylated second polysaccharide with the sulfhydryl group displayed by the polysaccharide-protein conjugate; to form a heterodimeric polysaccharide-protein conjugate of the type $Ps_2$-$spacer_2$-$Ps_1$-$spacer_1$-$PRO_1$, wherein $Ps_1$ and $Ps_2$ are bacterial polysaccharides and PRO is an immunogenic protein.

Thus, it is a purpose of the present invention to provide a polysaccharide-protein conjugate vaccine which delivers an effective amount of polysaccharide, without adverse effects due to the protein moiety such as pyrogenie response, swelling, and pain. It is an additional object of the present invention to provide a polysaccharide-protein conjugate vaccine having a high polysaccharide to protein ratio. An additional object of this invention is to provide a multivalent polysaccharide-protein conjugate vaccine having dissimilar polysaccharide entities such that a heterodimeric immunogen may be provided to induce an immune response against more than one cognate pathogen from a single vaccination.

DETAILED DESCRIPTION OF THE INVENTION

This invention is predicated on the fact that a polysaccharide, activated to display a pendant electrophile, such as a haloacetyl group, and then reacted with a protein, activated to display a nucleophilic group, such as a sulfhydryl, has many residual electrophilic groups after formation of the polysaccharide-protein conjugate. One embodiment of this invention takes advantage of these residual electrophilic groups by reacting a second polysaccharide, displaying a nucleophilic group, such as a sulfhydryl, with the already formed polysaccharide-protein conjugate. This series of reactions may be summarized as follows: $Ps_1$-$(BrAc)_n$+PRO-$(SH)_m \rightarrow$ PRO-S-$Ps_1$-$(BrAc)_{n-m}$; PRO-S-$Ps_1$-$(BrAc)_{n-m}$+$Ps_2$-$(SH)_x \rightarrow$ PRO-S-$Ps_1$-S-$Ps_2$; wherein n, m, and x define the molar amounts of the indicated reactant, and n>m, x≧n-m or, if x<n-m, then a capping step to remove residual readivesites is required.

In another embodiment, the first polysaccharide is activated to display a pendant nucleophile, such as a sulfhydryl, the protein is activated to display pendant electrophilic groups, such as haloacetyl groups, and the second polysaccharide is activated to display pendant electrophilic groups. Thus, this series of reactions may be summarized as follows: $Ps_1$-$(SH)_n$+PRO-$(BrAc)_m \rightarrow$ PRO-S-$Ps_1$-$(SH)_{n-m}$; PRO-S-$Ps_1$-$(SH)_{n-m}$+$Ps_2$-$(BrAc)_x \rightarrow$ PRO-S-$Ps_1$-S-$Ps_2$; with n, m, and x as defined above.

Naturally, the electrophilic and nucleophilic groups apppended to either the protein or polysaccharide moieties, may be other than the -BrAc or —SH groups shown For example, a maleimido group will react with the —SH group to provide the necessary conjugate.

In U.S. Pat. No. 4,695,624, Marburg et al., described polysaccharide-protein conjugates and a method of making such conjugates. The resulting polysaccharide-protein conjugates were of the form Ps—A—E—S—B—PRO, or of the form Ps—A'—S—E'—B'—PRO, wherein Ps represents a polysaccharide moiety, PRO represents an immunogenic protein, and A—E—S—B and A'—S—E'—B' represent atom chains linking the Ps and Pro moieties through the sulfur atom which is S in the chain. Thus, $spacer_1$ and $spacer_2$ of the conjugate of instant invention, which may be represented as $Ps_2$-$spacer_2$-$Ps_1$-$spacer_1$-PRO, are similar to the A—E—S—B and A'—S—E'—B' atom chains linking the Ps and PRO moieties of the 4,695,624 invention, which is hereby incorporated by reference.

The method of making the heterodimeric conjugate of this invention comprises separate activation of the Ps and PRO moieties. The Ps is functionalized with a spacer so as to exhibit either a pendant electrophile, such as a carbon substituted with a halogen leaving group, or a maleimido group, or a pendant nucleophile, such as a sulfhydryl, and then reacted with a separately activated PRO exhibiting a pendant nucleophile, such as a sulfhydryl or a pendant electrophile, such as a halogen leaving group or a maleimido group, respectively. All of the chemistry described in the 4,695,624 patent applies here with the improvement that a second Ps moiety is now activated in such a manner that it exhibits a pendant nucleophile, such as a sulfhydryl if the first Ps moiety was haloacetylated, or a pendant electrophile, such as a haloacetyl group, if the first Ps moiety exhibits pendant sulfhydryls. In this manner, the chemistry proceeds in a vectorial fashion to yield a multivalent conjugate immunogen of the $Ps_2$-$spacer_2$-$Ps_1$-$spacer_1$-PRO form, wherein $Ps_1$ and $Ps_2$ represent polysaccharides, and PRO represents a carrier polypeptide or protein.

In a preferred embodiment, the conjugate may be any stable Polysaccharide-polysaccharide-protein conjugate, coupled through bigeneric spacers containing a thioether group and primary amine, which form hydrolytically-labile covalent bonds with the polysaccharide and the protein.

The bigeneric spacers, $spacer_1$ and $spacer_2$ may be represented by the formulae A—E—S—B and A'—S—E'—B', as disclosed in U.S. Pat. No. 4,695,624. In a preferred embodiment of the invention, the spacers are selected from: —$CONH(CH_2)_5CONH(CH_2)_3$—O—$(CH_2)_4$—O—$(CH_2)_3$—$NHCOCH_2CH(COOH)$—S—$CH_2CONH(CH_2)_4CONH$—, —$CONH(CH_2)_3$—O—$(CH_2)_4$—O—$(CH_2)_3NHCO(CH_2)_5NHCOCH_2CH$—(COOH)—S—$CH_2CONH(CH_2)_4CONH$—, or a butane diaminyl-S-carboxymethyl-homocysteinyl complex. These spacers may be prepared as shown in examples 1 and 2 of this disclosure, and as described below.

In one embodiment of the invention, the preferred spacers may be prepared as follows:

In separate reactions, PRO, $Ps_1$, and $Ps_2$ are activated to display either pendant nucleophilic or electrophilic groups, with $Ps_1$ and $Ps_2$ being conversely activated and PRO and $Ps_1$ being conversely activated. A PRO-$Ps_1$ having residual haloacetyl residues is prepared, and then $Ps_2$ is added to form the PRO-$spacer_1$-$Ps_1$-$spacer_2$-$Ps_2$ conjugate of the invention.

Briefly, an immunogenic protein is reacted so as to display pendant nucleophilic moieties such as sulfhydryls by reaction with a thiolating agent, preferably N-acetylhomocysteine thiolactone, followed by removal of small molecules by a dialysis or ultrafiltration step which retain the protein, or by ultracentrifugation to pellet the derivatized protein, PRO', now bearing free sulfhydryl moieties.

The $Ps_1$ is derivatized to display pendant electrophilic moieties such as bromoacetyl moieties. Briefly, the $Ps_1$ is solubilized, reacted with carbonyl diimidazole, then with 1,4-butanediamine ($BuA_2$) dihydrochloride after which unreacted reagents are removed from the polysaccharide by dialysis or ultrafiltration. Then, the $Ps_1$-$BuA_2$ is reacted with p-nitrophenyl bromoacetate to generate $Ps_1'$ having pendant bromoacetyl moieties. The unreacted small molecules are removed by dialysis or ultrafiltration.

The PRO-$spacer_1$-$Ps_1$ portion of the conjugate is then formed by mixing the $Ps_1'$ with an appropriate quantity of PRO' to generate the PRO-$spacer_1$-$Ps_1$ conjugate having residual unreacted haloacetyl moeities avaiable on $Ps_1$ for reaction with $Ps_{2'}$.

In a preferred embodiment, $Ps_2'$ is prepared by solubilizing $Ps_2$, reacting the solubilized $Ps_2$ with carbonyldiimidazole, followed by addition of 2-(6-aminocaproyl)-4,9-dioxo-1,12-diamino dodecane (ACA-DODAD) naphthalene 1,5,disulphonic acid (NDSA) salt (ACA-DODAD-NDSA). The $Ps_2$-ACA-DODAD derivative is then reacted with S-acetyl mercapto succinic anhydride (SAMSA), to generate free sulfhydryl moieties on $Ps_2$ upon activation with hydroxylamine. The small molecules are removed by dialysis or ultrafiltration which retain the derivatized polysaccharide, $Ps_2'$.

The above description pertains to a conjugate such as is prepared in examples 1 and 2 below. However, an equivalent conjugate may be prepared by having the electrophilic moieties, such as haloacetyl groups, pendant on the protein and $Ps_2$, while $Ps_1$ is derivatized so as to exhibit pendant nucleophilic sites, such as sulfhydryl moieties.

It is desirable that the bigeneric spacers be chosen such that a thioether linkage is formed when a conjugate is made. This use of the thioether reflects the fact that this linkage is hydrolytically stable. By formulating the species chosen to comprise the spacer, it is possible to generate a uniquely identifiable amino acid containing the thioether linkage for purposes of amino acid analysis. Such amino acids as S-(carboxymethyl)-homocysteine, SCHMC, and S-(carboxymethyl)cysteamine, SCMCA, fulfill this requirement. Therefore, upon hydrolysis of a conjugate, these thioether containing amino acids will be detected in an amino acid analysis along with the constituent amino acids of the immunogenic protein moiety to which the polysaccharides were linked as disclosed and hereby incorporated by reference in U.S. Pat. No. 4,695,624, and in Marburg et al. [J.A.C.S. 108, 5282–5287 (1986)].

The polysaccharides of this invention may be any bacterial polysaccharide. Examples of such bacterial polysaccharides include *Streptococcus pneumoniae* (pneumococcal) types 1, 2, 3, 4, 5, 6 A, 6 B, 7 F, 8, 9 N, 9 V, 10 A, 11 A, 12 F, 14, 15 B, 17 F, 18 C, 19 A, 19 F, 20, 22 F, 23 F and 33 F, polysaccharides; Group B Streptococcus types Ia, Ib, II and III; *Haemophilus influenza*. (H. flu) type b polysaccharide; *Neisseria meningitidis* (meningococcal) groups A, B, C, X, Y, W135 and 29 E polysaccharides; and *Escherichia coli* K1, K12, K13, K92 and K100 polysaccharides. Particularly preferred polysaccharides, however, are those capsular polysaccharides selected from the group consisting of *Haemophilus influenzae* type b polysaccharide, such as described in Rosenberg et al, *J. Biol. Chem.*, 236, 2845–2849 (1961) and Zamenhof et al., *J. Biol. Chem.*, 203, 695–704 (1953); *Streptococcus pneumoniae* (pneumococcal) type 6 B or type 6 A polysaccharide, such as described in Robbins et al., *Infection and Immunity*, 26 No. 3, 1116–1122 (Dec 1979); pneumococcal type 19 F polysaccharide, such as described in C. J. Lee et al., *Reviews of Infectious Diseases*, 3, No. 2, 323–331 (1981); and pneumococcal type 23 F polysaccharide, such as described in O. Larm et al., *Adv. Carbohyd Chem. and Biochem.*, 33, 295–321, R. S. Tipson et al., ed., Academic Press, 1976. Many of these polysaccharides are obtainable from the ATCC as lyophilized bulk powders. A particularly preferred form of these polysaccharides is disclosed in application U.S. Ser. No. 646,573, in which size reduced highly purified forms of the polysaccharide are disclosed.

The proteins according to this invention are those of proven safety and demonstrable immunogenicity, but are not limited to any particular type. Suitable proteins include bacterial membrane proteins; any of various plant proteins, such as edestin or soybean trypsin inhibitor; viral protein subunits, such as hepatitis A or B, herpes gD or gC, Epstein-Bart or varicella zoster subunits; synthetic polypeptides: diphtheria toxoid; or tetanus toxoid, but are preferably Neisseria meningitidis (meningococcal) B serotype outer membrane proteins, which are T-cell stimulators. An example of these serotype proteins has been described in Helting et al., "Serotype Determinant Proteins of Neisseria Meningitidis", Actapath. Microbiol. Scand. Sect. C, 89, 69–78 (1981), and Frasch et al., J. Bact., 127, 973–981 (1976). Particularly preferred, is the outer membrane protein complex of Neisseria Meningitidis B or subunit proteins thereof.

In the process of the instant invention, the polysaccharides are covalently-modified, and the conjugate is formed by the steps of either:

(I)
(a) solubilizing a first and a second polysaccharide preparation in separate containers in a non-hydroxylic organic solvent; (b) activating the solubilized polysaccharide preparations with a bifunctional reagents; (c) reacting the first activated polysaccharide preparation with a bis-nucleophile, (d) functionalizing the first modified polysaccharide by reacting it with reagent generating electrophilic sites; (e) reacting a protein with a reagent generating nucleophilic groups; (f) reacting the first covalently-modified polysaccharide and the functionalized protein to form stable covalently-bonded polysaccharide-protein conjugate; (g) purifying the conjugate to remove unreacted polysaccharides and proteins; (h) activating second polysaccharide so as to be able to react with residual active sites on the stable covalently-bonded conjugate; (i) reacting the stable polysaccharide-protein conjugate with the second polysaccharide; and (j) isolating the multivalent conjugate free of residual unreacted reagents; or, (II)
(a) solubilizing a first and a second polysaccharide preparation in separate containers in a non-hydroxylic organic solvent; (b) activating the solubilized polysaccharide preparations with a bifunctional reagent; (c) reacting the first activated polysaccharide preparation with a bis-nucleophile, (d) functionalizing the first modified polysaccharide by reacting it with a reagent generating thiol groups; (e) reacting a protein with with a reagent generating electrophilic sites; (f) reacting the first covalently-modified polysaccharide and the functionalized protein to form a stable covalently-bonded polysaccharide-protein conjugate; (g) purifying the conjugate to remove unreacted polysaccharides and proteins; (h) activating a second polysaccharide so as to be able to react with residual active sites on the stable covalently-bonded conjugate; (i) reacting the stable polysaccharide-protein conjugate with the second polysaccharide; and (j) isolating the multivalent conjugate free of residual unreacted reagents.

The process of this invention also includes selection of a nucleophile or bis-nucleophile which will react with the activated polysaccharide to form a covalently-modified polysaccharide with pendant electrophilic sites or pendant thiol groups, thereby obviating the need to further functionalize the bis-nucleophile-modified polysaccharide prior to reacting the covalently-modified polysaccharide with the covalently-modified protein. Also, the functionalization of the protein to either electrophilic or nucleophilic form may be accomplished in more than one step according to the selection of reactants in these steps.

In a particularly preferred embodiment of this invention, the heterodimeric polysaccharide-protein conjugate may be prepared by the following method of either:

(I)
a) forming a polysaccharide-protein conjugate having residual haloacetyl groups which are reactive toward sulfhydryl groups;

b) succinylating an amino derivatized second polysaccharide with S-acetylmercapto succinic anhydride and deacetylating with hydroxyl amine to form sulfhydryl groups such that this polysaccharide will react with the polysaccharide-protein conjugate displaying residual haloacetyl groups;

c) displacing the halogen from one of the residual haloacetyl groups on the polysaccharide-protein conjugate with the liberated sulfhydryl on the second polysaccharide; or (II)
a) forming a polysaccharide-protein conjugate having residual sulfhydryl groups which are reactive toward a second haloacetylated polysaccharide;

b) haloacetylating a second polysaccharide such that this polysaccharide will react with the polysaccharide-protein conjugate displaying residual sulfhydryl groups;

c) displacing the halogen from the haloacetylated second polysaccharide with the sulfhydryl group displayed by the polysaccharide-protein conjugate; to form a heterodimeric polysaccharide-protein conjugate of the type $Ps_2$-$spacer_2$-$Ps_1$-$spacer_1$-$PRO_1$, wherein $Ps_1$ and $Ps_2$ are bacterial polysaccharides and PRO is an immunogenic protein.

A. PREPARATION OF THE POLYSACCHARIDE

This description applies equally to the $Ps_1$ and $Ps_2$ polysaccharide moieties, but the reader should take note that where $Ps_1$ is activated to exhibit a pendant electrophile as in haloacetylatfon, then $Ps_2$ is activated so as to exhibit a pendant nucleophile as in a sulfhydryl. The opposite is equally applicable with $Ps_1$ exhibiting the nucleophile and $Ps_2$ exhibiting the electrophile. In all cases, the PRO moiety is activated to exhibit an electrophile if $Ps_1$ exhibits a pendant nucleophile and a nucleophile if $Ps_1$ exhibits a pendant electrophile.

In the first step toward covalently-modifying the polysaccharide moieties, the solid polysaccharide must be solubilized. Since the nucleophilic alcoholic hydroxyl groups of a polysaccharide cannot compete, chemically, for electrophilic reagents in the presence of the hydroxyls of water in an aqueous solution, the polysaccharide is dissolved in non-aqueous (non-hydroxylic) solvents. Suitable solvents include dimethylformamide, dimethylsulfoxide (DMSO), dimethylacetamide, formamide, N,N'-dimethylimidazolidinone, and other similar polar, aprotic solvents. A preferred solvent for this purpose is DMSO.

In addition to the use of these solvents, conversion of the polysaccharides (e.g., the capsular polysaccharide of H. influenzae type b, which is a ribose-ribitol phosphate polymer, and of pneumococcal types 6 B, 19 F and 23 F), which have acid hydrogens, such as phosphoric acid mono- and diesters, into an appropriate salt form, these polysaccharides become readily soluble in the above solvents. The acidic hydrogens in these macromolecules may be replaced by large hydrophobic cations, such as tri- or tetra-($C_1$- to $C_5$)alkylammonium, 1-azabicyclo[2.2.2]octane,1,8-diazabicyclo [5.4.0]undec-7-ene or similar cations, particularly tri- or tetra-($C_1$- to $C_5$)alkylammonium, and the resultant tri- or tetraalkylammonium or similar salts of phosphorylated polysaccharides readily dissolve in the above solvents at about 17°–50° C., while being stirred for from one minute to one hour.

Partially-hydrolyzed *H. influenzae* type b polysaccharide has been converted into the tetrabutylammonium salt, then dissolved in dimethylsulfoxide (Egan et al., *J. Amer. Chem. Soc.*, 104, 2898 (1982)), but this product is no longer antigenic, and therefore useless for preparing vaccines. By contrast, solubilization of an intact, unhydrolyzed polysaccharide is accomplished herein by passing the polysaccharide through a strong acid cation exchange resin, in the tetraalkylammonium form, or by careful neutralization of the polysaccharide with tetraalkylammonium hydroxide, preferably by the former procedure. The viability of the polysaccharide for immunogenic vaccine use is thereby preserved.

Subsequent steps are directed at overcoming the other significant physico-chemical limitation to making covalent bonds to polysaccharides, including the lack of functional groups on the polysaccharides, other than hydroxyl groups, which are reactive enough with reagents commonly or practically used for functionalization of units with which bonding is desired. Activation of the polysaccharide to form an activated polysaccharide, reaction with bis-nucleophiles to form a nucleophile-functionalized polysaccharide, and functionalization with reagents generating either electrophilic sites or thiol groups, are all directed at covalently-modifying the polysaccharide and developing functional groups on the polysaccharide in preparation for conjugation.

The solubilized polysaccharide is activated by reaction with a bifunctional reagent at about 0°–50° C., while stirring for ten minutes to one hour, with the crucial weight ratio of activating agent to polysaccharide in the range of about 1:5 to 1:12. In the past, this activation has been accomplished by reaction of the polysaccharide with cyanogen bromide. However, derivatives activated with cyanogen bromide, which has a "proclivity" for vicinal diols, have shown transient stability during dialysis against a phosphate buffer. Therefore, while activation with cyanogen bromide is still possible according to the present invention, this reagent is poorly utilized in activation of polysaccharides and is not preferred. Instead, preferred bifunctional reagents for activating the polysaccharide include carbonic acid derivatives, 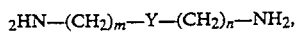 wherein $R^2$ and $R^3$ may be independently, azolyl, such as imidazolyl; halides; or phenyl esters, such as p-nitrophenyl, or polyhalophenyl.

Carbonyldiimidazole, a preferred reagent, will react with the hydroxyl groups to form imidazolylurethanes of the polysaccharide, and arylchloroformates, including, for example, nitrophenylchloroformate, will produce mixed carbonates of the polysaccharide. In each case, the resulting activated polysaccharide is very susceptible to nucleophilic reagents, such as amines, and is thereby transformed into the respective urethane.

The activated polysaccharide is then reacted with a nucleophilic reagent, such as an amine, in a gross excess of amine (i.e., for example, a 50- to 100-fold molar excess of amine vs. activating agent used), preferably a diamine, for example:

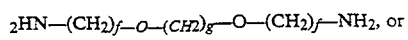

wherein m is 0 to 4, n is 0 to 3, and Y is $CH_2$, O, S, NR', $CHCO_2H$, and R' is H or a $C_1$- or $C_2$-alkyl such that if Y is $CH_2$, then both m and n cannot equal zero, and if Y is O or S, then m is greater than 1, and n is greater than 1 Also preferred are diamines of the formula:

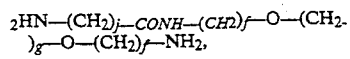

wherein $f \geq 2$, $g \geq 2$, and J=2 to 5.

The reaction is kept in an ice bath for from 15 minutes to one hour then kept for 15 minutes to one hour at about 17° to 40° C.

An activated polysaccharide, when reacted with a diamine, e.g., 1,4-butanediamine, would result in a urethane-form polysaccharide with pendant amines, which may then be further functionalized by acylating. Mixed carbonates will also readily react with diamines to result in pendant amine groups. The amine titer may be determined using a fluorescamine assay (Undefriend et al., Science 178:871–872 (1972)), and may be as high as 700 nmol/mg which is much higher than is achievable using cyanogen bromide activation (75–100 nmol/mg). The amine titer may be varied by varying the level of carbonic acid activating reagent used initially. Titers as high as 700 nmol/mg tend to attenuate the antigenicity of the polysaccharide, and lower titers of activation are preferable. NMR assays to determine functional group titer are preferable when possible.

Alternatively, the activated polysaccharide may be reacted with a nucleophile, such as a monohaloacetamide of a diaminoalkane, for example, 4-bromoacetamidobutylamine (see, W. B. Lawson et al., *Hoppe Seyler's Z. Physiol Chem.*, 349, 251 (1968)), to generate a covalently-modified polysaccharide with pendant electrophilic sites. Or, the activated polysaccharide may be reacted with an aminothiol, such as cysteamine (aminoethanethiol) or cysteine, examples of derivatives of which are well-known in the art of peptide synthesis, to produce a bisamino disulfide followed by reduction and dialysis, to generate a polysaccharide with pendant thiol groups. In both cases, no additional functionalization is necessary prior to coupling the covalently-modified polysaccharide to a modified "carrier" protein.

Further functionalization of the polysaccharide, if necessary, may take the form of either reacting the nucleophile-functionalized polysaccharide with a reagent to generate electrophilic sites, such as thiophilic sites, for example bromoacetyl moeities, or with a reagent to generate thiol groups, such as N-acetyl homocysteine thiolactone.

Reagents suitable for use in generating electophilic sites, include for example, those for acylating to α-haloacetyl or α-halopropionyl, derivative such as:

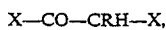

wherein R is H or $CH_3$; X is Cl, Br or I; and X' is nitrophenoxy, dinitrophenoxy, pentachlorophenoxy, pentafluorophenoxy, halide, O-(N-hydroxysuccinimidyl) or azido), particularly chloroacetic acid or α-bromopropionic acid, with the reaction being run at a pH of 8 to 11 (maintained in this range by the addition of base, if necessary) and at a temperature of about 0° to 35° C., for ten minutes to one hour. An amino-derivatized polysaccharide may be acylated with activated maleimido amino acids (see, O. Keller et al, *Helv. Chim. Acta.*, 58, 531 (1975)) to produce maleimido groups, such as

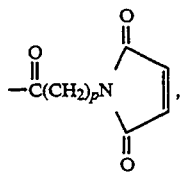

wherein p is 1 to 3; with a 2-haloacetyling agent, such as p-nitrophenylbromoacetate; or with an (α-haloketone carboxylic acid derivative, e.g.,

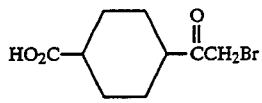

(Ber., 67, 1204, (1934)) in order to produce appropriately functionalized polysaccharides susceptible to thio substitution.

Reagents suitable for use in generating thiol groups include, for example, acylating reagents, such as thiolactones, e.g.,

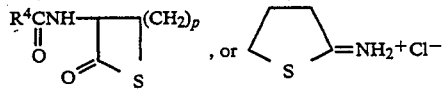

wherein $R^4$ is $C_1$- to $C_4$-alkyl or mono- or bicyclic aryl, such as $C_6H_5$ or $C_{10}H_{13}$, and p is 1 to 3; or

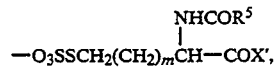

wherein m is 0 to 4, $R^5$ is $C_1$- to $C_4$-alkyl or $C_6H_5$, and X' is as defined above, followed by treatment with $HSCH_2CH_2OH$; or

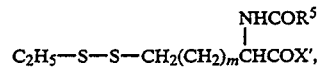

wherein m, $R^5$ and X' are as defined immediately above, followed by treatment with dithiothreitol; or $2HN(CH_2)_2$—S—S—$(CH_2)_2NH_2$, followed by treatment with dithiothreitol. Such reactions are carried out in a nitrogen atmosphere, at about 0° to 35° C. and at a pH of 8 to 11 (with base added, as necessary, to keep th pH within this range), for one to twenty-four hours. For example, an amino-derivatized polysaccharide may be reacted with

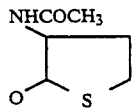

to produce an appropriately-functionalized polysaccharide.

By these steps then, covalently-modified polysaccharides of the forms, Ps—A—E*— or Ps—A'—SH—, wherein E* is

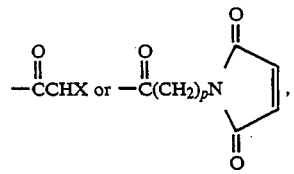

and A, A', R, X and p are as defined above, are produced.

B. PREPARATION OF THE PROTEIN

Separate functionalization of the protein to be coupled to the polysaccharide, involves reaction of the protein with one or more reagents to generate a thiol group, or reaction of the protein with one or more reagents to generate an electrophilic (e.g., a thiophilic) center.

In preparation for conjugation with an electrophilic-functionalized polysaccharide, the protein is reacted in one or two steps with one or more reagents to generate thiol groups, such as those acylating reagents used for generating thiol groups on polysaccharides, as discussed above. Thiolated proteins may also be prepared by aminating carboxy-activated proteins, such as those shown in Atassi et al., *Biochem et Biophys. Acta*, 670, 300, (1981), with aminothiols, to create the thiolated protein. A preferred embodiment of this process step involves the direct acylation of the pendant amino groups (i.e., lysyl groups) of the protein with N-acetyl-homocysteinethiolactone at about 0° to 35° C. and pH 8–11, for from five minutes to two hours, using equiweights of reactants.

When E'B'is

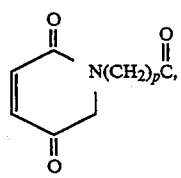

the conditions and method of preparing the functionalized protein are as discussed above for preparing the counterpart polysaccharide by reaction with activated maleimido acids.

In preparing for conjugation with a covalently-modified bacterial polysaccharide with pendant thiol groups, the protein is acylated with a reagent generating an electrophilic center, such acylating agents including, for example, $XCH_2CO$—X' and $XC(CH_3)H$—COX', wherein X and X' are as defined above; and

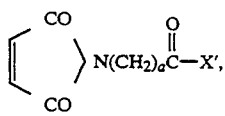

wherein X' is as defined above. Suitable proteins with electophilic centers also include, for example, those prepared by acylation of the pendant lysyl amino groups with a reagent, such as activated maleimido acids, for example,

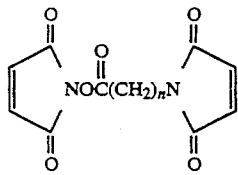

or by reacting the carboxy-activated protein with monohaloacetyl derivatives of diamines. In both preparation reactions, the temperature is from 0° to 35° C. for from five minutes to one hour and the pH is from 8 to 11.

C. FORMATION OF THE CONJUGATE

-continued

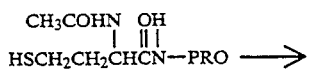

wherein a functionalized polysaccharide which has been reacted with 4-bromoacetamidobutylamine is reacted with a protein which has been reacted with N-acetyl-homocysteinethiolactone, to form a conjugate, and subsequently purified away from reactants. Next, residual bromo groups are displaced from the conjugate by $Ps_2$ functionalized by reaction with

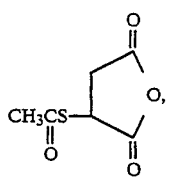

followed by reaction with hydroxylamine, to display a pendant sulfhydryl moieties. This would form the conjugate:

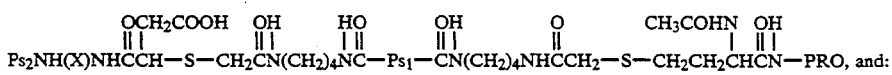

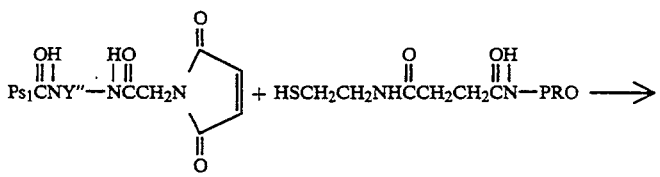

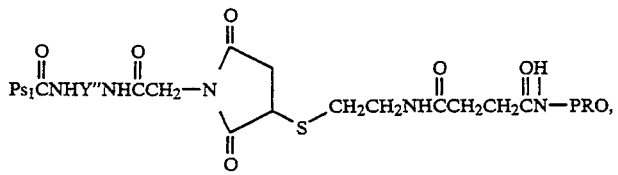

Formation of the conjugate is then merely a matter of reacting the covalently-modified $Ps_1$ polysaccharide having pendant electrophilic centers with a protein having pendant thiol groups at a pH of 7 to 9, in approximate equiweight ratios, in a nitrogen atmosphere, for from six to twenty-four hours at from about 17° to 40° C., to give a covalent conjugate. Examples of such reactions include:

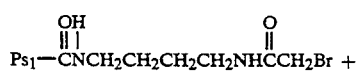

where Y" is a $C_2$-$C_8$alkyl radical, wherein an amino-derivatized polysaccharide which has been reacted with activated maleimido acids is reacted with a carboxy-activated protein which has been aminated with an aminothiol, to form a conjugate. Subsequent to purification of this conjugate, a $Ps_2$ species, activated to exhibit a pendant sulfhydryl to yield a species such as:

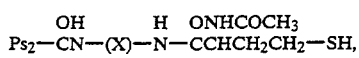

wherein X is a $C_2$-$C_8$ alkyl, to yield the conjugate:

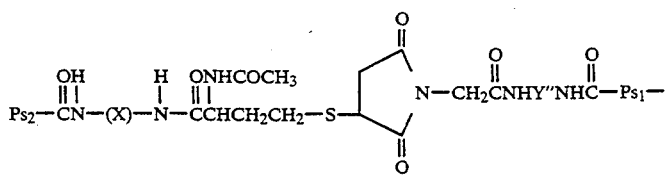

-continued

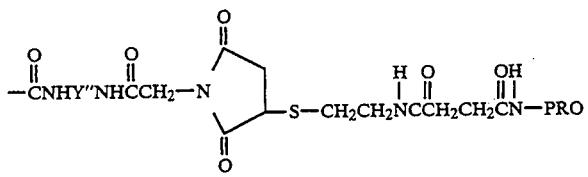

Similarly, a covalently-modified Ps₁ polysaccharides with pendant thiol groups may be reacted with a protein having pendant electrophilic centers to give a covalent conjugate. An example of such a reaction is:

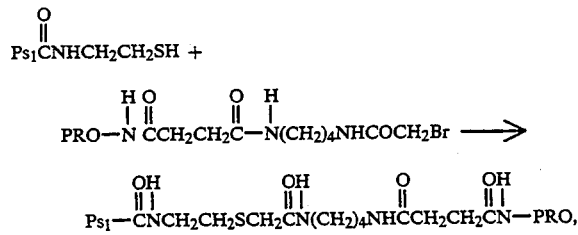

wherein an activated polysaccharide which has been reacted with an aminothiol is reacted with a carboxy-activated protein which has been reacted with monohaloacetyl derivatives of a diamine, to form a conjugate. This conjugate is purified away from reactants, and a Ps₂ polysaccahride species, activated to exhibit a pendant electrophilic site by reaction with, for example, 4-bromoacetamidobutylamine, is reacted with residual sulfhydryls displayed by the activated Ps₁ to form a multivalent conjugate of the form:

charides, using the covalency assay for the bigeneric spacer (see below) as a method of following the desired biological activity.

The further separation of reagents may be accomplished by size-exclusion chromatography in a column, or in the case of very large, non-soluble proteins, such as *N. meningitidis* B serotype outer membrane protein, this separation may be accomplished by ultracentrifugation.

D. ANALYSIS TO CONFIRM COVALENCY

Analysis of the conjugate to confirm the covalency, and hence the stability of the conjugate, is accomplished by hydrolyzing (preferably with 6N HCl at 110° C. for 20 hours) the conjugate, then quantitatively analyzing for the amino acid of the hydrolytically-stable spacers containing the thioether bond and constituent amino acids of the protein. The contribution of the amino acids of the protein may be removed, if necessary, by comparison with the appropriate amino acid standard for the protein involved, with the remaining amino acid value reflecting the covalency of the conjugate, or the amino acids of the spacers may be designed to appear outside the amino acid standard of the protein in the analysis. The covalency assay is also useful to monitor purifica-

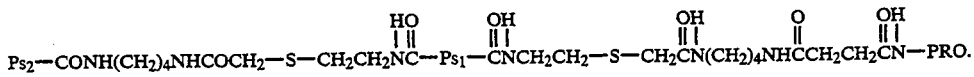

Should the electrophilic activity of an excess of haloacetyl groups need to be eliminated, reaction of the conjugate with a low molecular weight thiol, such as tion procedures to mark the enhancement of concentration of the biologically-active components. In the above examples, hydrolysis of

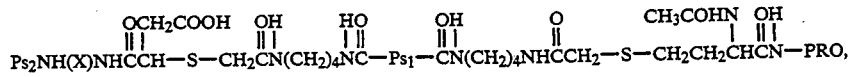

N-acetylcysteamine, will accomplish this purpose. Use of this reagent also allows confirmation accounting of the haloacetyl moieties used (see Section D), because the S-carboxymethylcysteamine which is formed may be uniquely detected by the method of Spackman, Moore and Stein.

The conjugate is then centrifuged at about 100,000×G using a fixed angle rotor for about two hours at about 1° to 20° C., or are submitted to any of a variety of other purification procedures, including gel permeation, ion exclusion chromatography, gradient centrifugation, or other differential adsorption chromatography, to remove non-covalently-bonded polysacresults in the release of S-carboxymethylhomocysteine,

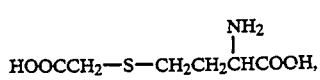

and the release of

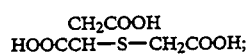

while hydrolysis of

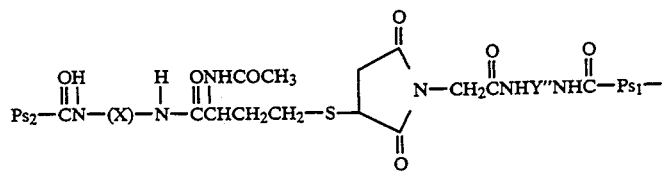

-continued

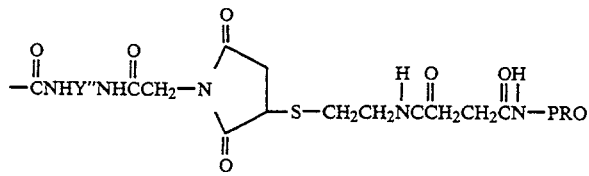

results in the release of the aminodicarboxylic acid,

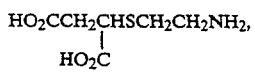

and the release of by cleavage of the Ps2-spacer2-Ps1-spacer1-PRO molecule at peptide linkages and other hydrolyrically-unstable bonds. Chromatographic methods, such as those of Spackman, Moore, and Stein, may then be conveniently applied and the ratio of amino acid constituents determined.

E. APPLICATIONS

One or more of the conjugates of this invention may be used in mammalian species for either active or passive protection prophylactically or therapeutically against bacteremia caused by the cognate organism, such as, in the preferred embodiments of this invention, *Haemophilus influenzae* type b and *Streptococcus pneumoniae* organisms. Active protection may be accomplished by injecting an effective amount (a quantity capable of producing measurable amounts of antibodies, e.g., about 2 to 50 μg) of the least immunogenic polysaccharide in the conjugate per dose. Whole antiserum, obtained from animals previously dosed with the conjugate or conjugates, or globulin or other antibody-containing fractions of said antisera, with or without a pharmaceutically-acceptable carrier, such as aseptic saline solution, may be used to provide passive protection. Such globulin is obtained from whole antiserum by chromatography, salt or alcohol fractionation or electrophoresis. Passive protection may also be accomplished by standard monoclonal antibody procedures or by immunizing suitable mammalian hosts. The use of an adjuvant (e.g., alum) is also intended to be within the scope of this invention.

In a preferred embodiment of this invention, the conjugate is used for active immunogenic vaccination of humans, especially infants and children. For additional stability, these conjugates may also be lyophilized in the presence of lactose (for example, at 20 μg/ml of H. flu. polysaccharide/4 mg/ml lactose or 50 μg/ml of pneumococcal polysaccharide/10 mg/ml lactose) prior to use.

A preferred dosage level is an amount of each of the conjugates or derivative thereof to be administered corresponding to about 25 μg of polysaccharide in the conjugate form for the pneumococcal polysaccharides and about 10 μg of polysaccharide in the conjugate form of the *H. influenzae* type b polysaccharide in a single administration. If necessary, an additional one or two doses of conjugate or derivative thereof in an amount corresponding to about 10 μg of the less immunogenic polysaccharide in the conjugate form, may also be administered.

The invention is further defined by reference to the following examples, which are intended to be illustrative and not limiting.

EXAMPLE 1

Preparation of OMPC-PRP-PnPs6A Heterodimeric Conjugate

Preparation of OMPC-PRP Conjugate having Residual Reactive Moieties:

A. PRP DERIVATIZATION:

Oxalic acid (9 μmg) was dissolved in 5 mL water. In a separate container, PRP (600 mg) was dissolved in 18 mL water. The dissolved PRP was then added slowly to the oxalic acid solution. Th pH was adjusted to 7.17 with tetra-N-butyl ammonium hydroxide solution. Insoluble calcium oxalate was filtered off and the PRP containing filtrate was transferred to a rotary evaporator, 21 mL of DMF was added, and the volume bought to 21 mL. This replacement of water for DMF was repeated with 5 additions and concentrations of 21 mL DMF.

The solution was blanketed with $N_2$, and carbonyldiimidazole (CDI) (0.067 g in 1.7 mL of DMF) was added and the reaction aged for 35 minutes. 1,4-Butandiamine dihydrochloride was dissolved in 144 mL water, the pH adjusted to 10.4 with 50% NaOH, cooled to 15° C., and added slowly to the PRP-CDI solution. The temperature was raised to 27° C. and the solution aged for 15 minutes. The pH was adjusted to 7.05 with phosphoric acide (1.8 mL).

The sample was diafiltered using a 10,000 dalton cutoff Amicon hollow fiber membrane against 1.5 L of 0.1M phosphate buffer, pH 7, to a final volume of 40 mL. $Na_2B_4O_7.10H_2O$ (0.4 g) was added and the pH was adjusted to 9.2 with sodium hydroxide. The solution was cooled to 2°–10° C., and bromoacetyl chloride (0.54 mL) and NaOH ( 3.7 mL of 5N) was added. The solution was stirred, the pH adjusted to 7 and diafiltered against 2 L of water to yield a final volume of 70 mL. NMR analysis revealed the presence of 19.9% bromoacetyl loading.

B. OMPC THIOLATION

Aqueous OMPC suspension (100 mL, 3 mg/mL) was diafiltered against borate buffer, pH 11.3 (500 mL) to a final volume of 40 mL. To this suspension was added EDTA (171 mg) and DTT (33 mg) as solids, followed by N-acetyl homocysteine thiolactone (268 mg), followed by two additional charges of thiolactone at one hour intervals (2×134 mg).

The thiolated OMPC was diafiltered against 0.1M phosphate buffer, pH 11.3 (1.6 L), to give a final volume of 55 mL. Lowry assay gave a protein concentration of 1.6 mg/ml, and by Ellman assay, a SH/protein ratio of 0.18 μmoles/mg was calculated.

C. CONJUGATION OF BROMOACETYL-PRP AND THIOLATED OMPC

Derivatized PRP (80 mg) was dissolved in degassed 0.1M phosphate buffer pH 8 (250 mL). Thiolated OMPC was slowly added to the PRP solution and the pH was maintained at 8 by the addition of of 0.1M potassium phosphate (24 mL). After 18 hours of conjugation time, an 8 mL sample was removed, centifuged (2 hours, 42,000 rpm), and resuspended in water. The pellet was resolubilized in water and recentrifuged two additional times, to remove unconjugated derivatized PRP which remains in the supernatant.

D. PREPARATION OF REACTIVE PnPs6A

One gram of *Streptococcus pneumoniae* 6A polysaccharide (PnPs6A) was covered with about 25 mL water and stirred until dissolved. This solution was added to about 30 mL column packed with Dowex 50×2, tetrabutylamine form ($Bu_4N^+$). The column was eluted with water and the effluent was lyophilized to yield about 1.12 grams of PnPs6A-$Bu_4N^+$.

PnPs6A-$Bu_4N^+$ (625 mg) was covered with about 20 mL dimethylformamide (DMF, dried, degassed) and stirred for about 40 minutes. Carbonyldiimidazole (72 mg) was added and the mixture was stirred for an additional hour, followed by addition of 625 mg 2-(6-aminocaproyl)4,9-dioxo-1,12-diamino dodecanenaphthalene-1,5-disulphonic acid salt (ACA-DODAD-NDSA) in 20 mL water at 5° C. pH 10.39. The mixture was stirred on ice for about 30 minutes and then at room temperature for an additional hour.

The solution was dialyzed for about 16 hours against 4 L pH 7, 0.1M phosphate buffer, followed by another 3.5 hours against a fresh 4 L of the same buffer. Dialysis against 30 L of water for 25 hours followed by an additional 20 hours against 4 L of fresh water. The dialyzed sample was lyophilized, resolubilized, and passed through a 30 mL Dowex 50×2 column, $Bu_4N^+$ form. A 0.39 g eluate fraction was analyzed by NMR and found to have ACA-DODAD $Bu_4N^+$ resonances which indicates covalency, and about 76 nanomoles ACA/mg of material by amino acid analysis for aminocaproic acid.

PnPs6A-ACA-DODAD-$Bu_4N^+$ (193 mg) was dissolved in 10 mL of pH 7.2, 0.1M phosphate buffer. 177 mg of of S-acetyl mercapto succinic anhydride (SAMSA) was added in 1 mL of DMF. The pH rapidly decreased to 4.6, and the solution was basified to pH 7.1 by addition of 0.5M NaOH. The mixture was stirred at room temperature for 1 hour. An additional sample of 77 mg SAMSA in DMF was added and the sample was again basified by addition of NaOH, followed by stirring for 40 minutes. The sample was dialyzed against 16 L 0.1M phosphate buffer, pH 7.25 for 5 hours, then against 4 L of fresh buffer overnight, and then against 30 L of water for about 7 hours The sample was then lyophilized to obtain 160 mg of product, which was confirmed, by NMR evaluation, to be SAMSA derivatized.

E. CONJUGATION OF THE PRP-OMPC HAVING RESIDUAL REACTIVE MOIETIES WITH REACTIVE PnPs6A

PRP-OMPC conjugate prepared above (8 mL), containing 6.7 mg protein, was resuspended by sonication, followed by centrifugation at 43,000 rpm, 4° C. for 2 hours. The pellet was Dounce homogenized in 2 mL pH7 0.1M phosphate buffer with 2 mM EDTA. The sample was aged at 4° C. for 60 hours. $NH_2OH\cdot HCl$ (13 mg) was then added, along with 4 mg EDTA disodium salt and the pH was adjusted to 8.2 with 5 N NaOH having 2 M NaCl dissolved therein. The sample was degassed and then 20 mg of the PnPs6A-ACA-DODAD-SAMSA from B. was added. The sample was mixed end-over-end for hours, resulting in the formation of a gelatinous mix. The gelatinous material was removed by filtration through Whatman #1 paper and the sample was aged for about 12 hours. The sample was then centrifuged at 43,000 rpm for 2 hours 4° C. to remove unconjugated PnPs6A which remains in the supernatant.

Water (10 mL) was added to the pellet which was dislodged and mixed followed by recentrifugation. The pellet was dissolved in 1 mL. A rate nephelometric assay directed at detection of PnPs6A was positive. An assay for methyl pentose revealed the presence of 81 μg of PnPs6A per ml of sample. A protein assay revealed the presence of 460 μg/ml. Thus, the mass ratio of PnPs6A to OMPC in the sample was 0.18.

EXAMPLE 2

PREPARATION OF OMPC-PnPs6A-PRP HETERODIMERIC CONJUGATE

A. THIOLATION OF OMPC

A 10 mL solution of OMPC containing 3.8 mg protein/mL was centrifuged at 43,000 rpm for 2 hours at 4° C. The pellet was resuspended by Dounce homogenization in 4.2 mL thiolation mix (0.63 mg EDTA, 12 mg DTT in 7 mL pH 11, 0.1M borate buffer). The sample was degassed, and 40 mg of N-acetylhomocysteinethiolactone was added. The sample was aged under a nitrogen atmosphere for 19 hours. $KH_2PO_4$ (2.5 mL), 1M buffer, was then added and the sample volume adjusted to 10 mL with 0.1M pH 7 phosphate buffer. The sample was centrifuged for 2 hours at 43,000 rpm. at 5° C., and the pellet was resuspended in 10 mL 0.1M phosphate buffer, pH 8 and recentrifuged as before.

The pellet was resuspended in 4.5 mL pH 8 0.1M phosphate buffer. 0.1 mL of the sample was taken for Ellman assay which revealed the presence of of a total of 6.08 μmoles sulfhydryl groups.

B. PREPARATION OF BROMOACETYL-BUTANEDIAMINE-PnPs6A (PnPs-$BuA_2$-BrAc)

PnPs6A (5 grams) was dissolved in 150 mL water and then applied to a 55 mL Dowex 50×2 (200–400 $Bu_4N^+$ form) column. The PnPs6A-$Bu_4N^+$ was eluted and 2 fractions were collected, comprising a total of 5.54 g of the salt.

PnPs6A-$Bu_4N^+$ (256 mg) was covered with 8 mL DMF and stirred at room temperature for about 40 minutes. Carbonyldiimidazole (29 mg) was then added and stirring continued for an additional hour and 20 minutes. Butane diamine.2HCl (280 mg) dissolved in 10 mL of water, pH 10.1 was added on ice and stirring was continued for another 0.5 hours on ice. Thereafter, the sample was stirred for an additional hour at room temperature. The sample was subsequently dialyzed against 16 L of 0.1M phosphate pH 7.1 buffer for 18 hours, then against 4 L 0.01M phosphate buffer pH 6.85 for 7 hours followed by 21 hours against 30 L of water. The dialyzed sample was then lyophilized to yield 184 mg, which upon analysis by NMR revealed the presence of 1 $BuA_2$ per every 3 PnPs6A monomer units.

PnPs6A-$BuA_2$ (177 mg) was dissolved in 20 mL pH 9, 0.1M phosphate buffer, and 158 mg of p-nitrophenyl bromoacetate in 6 mL acetonitrile was then added. The reaction was allowed to proceed at 4° C. for 17 hours, following which the sample was dialyzed against 30 L water for 6.5 hours, then against 4 L water for 1 hour, then against 30 L water for 16 hours, and then against 4 L water for an additional 8 hours. The dialyzed sample was lyophlized and a total of 164 mg of product was recovered. NMR revealed a change from the starting material such that the two —CH$_2$CH$_2$— upfield multiplets collapsed into one multiplet.

C. CONJUGATION OF THE THIOLATED OMPC WITH PnPS6A-BuA$_2$-BrAc

The thiolated OMPC from step A. was mixed with 35 mg of bromoacetylated polysaccharide from step B. The reaction was degassed and aged for 18.5 hours at room temperature. Water was added to a final voulume of 10 mL, the viscous solution was vortexed and the centrifuged at 5° C. for 2 hours at 43,000 rpm. The pellet was resuspended, Dounce homogenized and recentrifuged as before. This series was repeated three times. The final pellet was resuspended in about 10 mL of water. Protein analysis revealed 990 μg/ml. Methyl pentose assay revealed the presence of 266 μg/ml PnPs6A, yielding a polysaccharide to protein mass ratio of 0.27.

D. PREPARATION OF PRP-ACA-DODAD-SAMSA

Polyribosyl-ribitol-phosphate (PRP) (2.33 g) was covered with about 45 mL water. The solubilized polysaccharide was then passed through a 35 mL Dowex 50×2 Bu$_4$N+ column. The effluent was freeze-dried and a total of 2.71 g of PRP-Bu$_4$N+ was recovered.

PRP-Bu$_4$N+ (606 mg) was covered with 17 mL DMF and stirred for three hours until in solution. 73 mg of carbonyl diimidazole was then added and the stirring continued for 35 minutes. This solution was then mixed with 750 mg of ACA-DODAD-NDSA in 20 mL of water pHed to 10.32 with 5 N NaOH. The solution was cooled on ice for 30 minutes, then warmed to room temperature and transferred to a Spectrapor 2 dialysis tube. Dialysis was conducted against 4 L 0.1M phosphate buffer pH 7.17 for 18.5 hours, then against 4 L 0.1M phosphate pH 7.07 for 8 hours, then against another 4 L for 16 hours, then against 16 L 0.025M buffer pH 7.17 for 4.5 hours, and finally against 32 L water for 19.5 hours. The sample was then freeze-dried to yield 0.38 g of material. NMR revealed the presence of 1 ACA-DODAD unit per every 6 PRP monomer units.

PRP-ACA-DODAD (100 mg) was dissolved in 100 ml 0.1M phosphate, 2 mM EDTA, pH 7.5, followed by addition of 100 mg SAMSA. The sample was mixed end-over-end at 4° C. for 2 hours, then the pH was adjusted from 5.6 to 6.5 with 1 N NaOH. An additional 45 mg SAMSA was added and the sample was mixed for about 16 hours, end-over-end. The "soapy" sample was dialyzed against 16 L phosphate buffer, pH 7.2 for 6 hours then against 4 L water for 21 hours, followed by an additional 25.5 hours against 30 L of water. The sample was freeze-dried to yield 71 mg of product. An aliquot of the sample was analyzed as follows: A soltion of 69 mg NH$_2$OH.HCl and 18 mg EDTA.Na$_2$ in 10 mL 0.1M phosphate buffer pH 8 was prepared (final pH=6.5). To 2 mg of the PRP-ACA-DODAD-SAMSA sample was added 1 mL of this solution. The sample was degassed and 5 μL of 5M NaOH was added. The sample was aged under nitrogen for 35 minutes, at which point an Ellman assay revealed the presence of 0.14 μmoles sulfhydryl/mg of sample, which was about 33% of the expected theoretical yield.

E. CONJUGATION OF PnPs6A-OMPC WITH PRP-ACA-DODAD-SAMSA

A solution of 10 mL phosphate buffer, pH 8 containing 10 mg NH$_2$OH.HCl (14 mM) and 38 mg EDTA (10 mM) was prepared. PRP-ACA-DODAD-SAMSA (15 mg) was dissolved in 2 mL of the hydroxylamine solution, and to this was added 3 mL of the PnPs6A-OMPC conjugate (totaling about 800 μg PnPs6A and about 3 mg protein). To this mixture was added an additional 1 mL of the hydroxylamine solution (final concentration hydroxylamine 2 mM, for a total of 14 μmoles, and 2 mM EDTA). The sample was degassed and aged under an atmosphere of nitrogen for about 66 hours. The sample was topped with water and centrifuged at 43,000 rpm for 2 hours at 4° C., to remove unconjugated derivatized PRP.

The pellet was resuspended in water and then recentrifuged as before. The final conjugate was resuspended in a total of 4 mL water. Aliquots of the sample were assayed, revealing the presence of 62 μg/ml PRP in the centrifugation supernatant, and 155 μg/ml in the pellet. The mass ratio of PRP/OMPC was found to be 0.21 in the pellet, and PnPs6A/OMPC=0.27.

EXAMPLE 3

Immunogenicity of the PnPs6A-PRP-OMPC conjugate

The immunogenicity of the PnPs6A-PRP-OMPC conjugate was tested in a chinchilla model. The conjugate was adsorbed onto aluminum hydroxide and administered intramuscularly at 0 and 4 weeks at a dose of:

| PnPs6A μg | PRP μg |
| --- | --- |
| 2 | 3.09 |
| 0.4 | 0.62 |
| 0.08 | 0.12 |

The animals were bled at 0, 2, 4, 6, 8 weeks and the anti-PnPs6A and anti-PRP antibody titers were compared with placebo (aluminum hydroxide alone) titers. High titers of both anti-PRP and anti-PnPs6A were generated, as measured by radioimmunoassay, at all levels of conjugate administered.

EXAMPLE 4

Protection of chinchillas against pneumococcal infection following administration of PnPs6A-PRP-OMPC conjugate Using aggresive, direct middle ear challenge with live virulent *Streptococcus pneumoniae* type 6A, animals inoculated with the PnPs6A-PRP-OMPC immunogen were protected from otitis media as follows:

| Dose | No. Animals with no otitis media |
| --- | --- |
| 2 μg | 4/5 |
| 0.4 μg | 1/5 |
| 0.08 μg | 3/5 |
| 0 | 1/10 |

EXAMPLE 5

Preparation of *Neisseria meningitidis* B11 Serotype 2 OMPC

A. Fermentation

1. *Neisseria meningitidis* Group B11

A tube containing the lyophilized culture of *Neisseria meningitidis* (obtained from Dr. M. Artenstein, Walter Reed Army Institute of Research (WRAIR), Washington, D.C.) was opened and Eugonbroth (BBL) was added. The cul agar slants and incubated at 37° C. with 5% $CO_2$ for 36 hours, at which time the growth was harvested into 10% skim milk medium (Difco), and aliquots were frozen at −70° C. The identity of the organism was confirmed by agglutination with specific antiserum supplied by WRAIR, and typing serum supplied by Difco.

A vial of the culture from the second passage was thawed and streaked onto 10 Columbia Sheep Blood agar plates (CBAB-BBL). The plates were incubated at 37° C. with 5% $CO_2$ for 18 hours after which time the growth was harvested into 100 mL of 10% skim milk medium, aliguots were taken in 0.5 mL amounts and frozen at −70° C. The organism was positively identified by agglutination with specific antiserum, sugar fermentation and gram stain.

A vial of the culture from this passage was thawed, diluted with Mueller-Hinton Broth and streaked onto 40 Mueller-Hinton agar plates. The plates were incubated at 37° C. with 6% $CO_2$ for 18 hours after which time the growth harvested into 17 mL of 10% skim milk medium, aliquotted in 0.3 mL amounts and frozen at −70° C. The organism was positively identified by Gram stain, agglutination with specific antiserum and oxidase test.

2. Fermentation and collection of cell paste a. Inoculum Development- The inoculum was grown from one frozen vial of Neisseria memingitidis Group B, B-11 from above (passage 4). Ten Mueller-Hinton agar slants were inoculated, and six were harvested approximately 18 hours later, and used as an inoculum for 3 250 mL flasks of Gotschlich's yeast dialysate medium at pH 6.35. The O.D.$_{660}$ was adjusted to 0.18 and incubated until the $OD_{660}$ was between 1 and 1.8. 1 mL of this culture was used to inoculate each of 5 2 L. Erlenmeyer flasks (each containing 1 liter of medium; see below) and incubated at 37° C. in a shaker at 200 rpm. The O.D. was monitored at hourly intervals following inoculation. 4 liters of broth culture, at an O.D.$_{660}$ of 1.28 resulted.

70 Liter Seed Fermenter- Approximately 4 liters of seed culture was used to inoculate a sterile 70-liter fermenter containing about 40 liters of complete production medium (see below). The conditions for the 70-liter fermentation included 37° C., 185 rpm with 10 liters/minute air sparging and constant pH control at about pH 7.0 for about 2 hours. For this batch, the final O.D.$_{660}$ was 0.732 after 2 hours.

800-Liter Production Fermenter

Approximately 40 liters of seed culture were used to inoculate a sterile 800 liter fermenter containing 568.2 liters of complete production medium (see below). The batch was incubated at 37° C., 100 rpm with 60 liters/-minute air sparging and constant pH control at pH 7.0. For this batch, the final O.D. was 5.58 thirteen hours after inoculation.

3. Complete Medium for Erlenmeyer flasks and 70-and 800-liter fermenters

| Fraction A | |
|---|---|
| L-glutamic acid | 1.5 g/liter |
| NaCl | 6.0 g/liter |
| $Na_2HPO_4$.anhydrous | 2.5 g/liter |
| $NH_4Cl$ | 1.25 g/liter |
| KCl | 0.09 g/liter |
| L-cysteine HCl | 0.02 g/liter |

Fraction B (Gotschlich's Yeast Dialysate)

1280 g of Difco Yeast Extract was dissolved in 6.4 liters of distilled water. The solution was dialyzed in 2 Amicon DC-30 hollow fiber dialysis units with three H10SM cartridges. 384 g $MgSO_4.7\text{-}H_2O$ and 3200 g dextrose were dissolved in the dialysate and the total volume brought to 15 liters with distilled water. The pH was adjusted to 7.4 with NaOH, sterilized by passage through a 0.22 μ filter, and transferred to the fermenter containing Fraction A.

For the Erlenmeyer flasks: 1 liter of Fraction A and 25 mL of Fraction B were added and the pH was adjusted to 7.0–7.2 with NaOH.

For the 70 liter fermenter: 41.8 liters of Fraction A and 900 mL of Fraction B were added and the pH was adjusted to 7.0–7.2 with NaOH.

For the 800 liter fermenter: 553 liters of Fraction A and 15.0 liters of Fraction B were added and the pH was adjusted to 7.1–7.2 with NaOH.

d. Harvest and Inactivation

After the fermentation was completed, phenol was added in a separate vessel, to which the cell broth was then transferred, yielding a final phenol concentration of about 0.5%. The material was held a room temperature with gentle stirring until the culture was no longer viable (about 24 hours).

e. Centrifugation

After about 24 hours at 4° C., the 614.4 liters of inactivated culture fluid was centrifuged through Sharples continuous flow centrifuges. The weight of the cell paste after phenol treatment was 3.875 kg.

B. OMPC Isolation

Step 1. Concentration and diafiltration

The phenol inactivated culture was concentrated to about 30 liters and diafiltered in sterile distilled water using 0.L micro-hollow fiber filters (ENKA).

Step 2. Extraction

An equal volume of 2× TED buffer [0.1M TRIS 0.01M EDTA Buffer, pH 8.5, with 0.5% sodium deoxycholate] was added to the concentrated diafiltered cells. The suspension was transferred to a temperature regulated tank for OMPC extraction at 56° C. with agitation for 30 minutes.

The extract was centrifuged at about 18,000 rpm in a Sharples continuous flow centrifuge at a flow rate of about 80 mL/minute, at about 4° C. The viscous supernatant was then collected and stored at 4° C. The extracted cell pellets were reextracted in TED buffer as described above. The supernatants were pooled and stored at 4° C.

Step 3. Concentration by Ultrafiltration

The pooled extract was transferred to a temperature regulated vessel attached to AG-Tech 0.1 micron polysulfone filters. The temperature of the extract was held at 25° C. in the vessel throughout the concentration process. The sample was concentrated tenfold at an average transmembrane pressure of between 11 and 24 psi.

Step 4. Collection and Washing of the OMPC

The retentate from Step 3 was centrifuged at about 160,000×g (35,000 rpm) at about 70° C. in a continuous flow centrifuge at a flow rate between 300 to 500 mL/minute, and the supernatant was discarded.

The OMPC pellet was suspended in TED Buffer (190 mL buffer; 20 mL/g pellet) Step 2 and Step 4 were repeated twice (skipping Step 3).

Step 5. Recovery of OMPC Product

The washed pellets from Step 4 were suspended in 100 mL distilled water with a glass rod and a Dounce homogenizer to insure complete suspension. The aqueous OMPC suspension was then filter sterilized by passage through a 0.22 μ filter, and the TED buffer was replaced with water by diafiltration against sterile distilled water using a 0.1 μ hollow fiber filter.

EXAMPLE 6

Preparation of H. Influenzae Type b Capsular Polysaccharide (PRP)

Inoculum and Seed Development

A Stage: A lyophilized tube of *Haemophilus influenzae* type b, (cultured from Ross 768, received from State University of New York) was suspended in 1 mL of sterile Haemophilus inoculum medium (see below) and this suspension was spread on 9 Chocolate Agar slants (BBL). The pH of the inoculum medium was adjusted to 7.2±0.1 (a typical value was pH 7.23) and the medium solution was sterilized prior to use by autoclaving at 121° C. for 25 minutes. After 20 hours incubation at 37° C. in a candle jar, the growth from each plate was resuspended in 1–2 mL Haemophilus inoculum medium, and pairs of slants were pooled.

| Haemophilus Inoculum Medium | |
|---|---|
| Soy Peptone gm/liter | 10 |
| NaCl gm/liter | 5 |
| $NaH_2PO_4$ gm/liter | 3.1 |
| $Na_2HPO_4$ gm/liter | 13.7 |
| $K_2HPO_4$ gm/liter | 2.5 |
| Distilled Water | To Volume |

The resuspended cells from each pair of slants was inoculated into three 250 mL Erlenmeyer flasks containing about 100 mL of Haemophilus Seed and Production medium. The 250 mL flasks were incubated at 37° C. for about 3 hours until an $OD_{660}$ of about 1.3 was reached. These cultures were used to inoculate the 2 liter flasks (below).

B Stage: 2 Liter non-baffled Erlenmeyer flasks- 5 mL of culture from "A stage" (above) were used to inoculate each of five two-liter flasks, each containing about 1.0 liter of complete Haemophilus seed and production medium (see below). The flasks were then incubated at 37° C. on a rotary shaker at about 200 rpm for about 3 hours. A typical $OD_{660}$ value at the end of the incubation period was about 1.0.

| Complete Haemophilus Seed And Production Medium | |
|---|---|
| | Per liter |
| $NaH_2PO_4$ | 3.1 g/L |
| $Na_2HPO_4$ | 13.7 g/L |
| Soy Peptone | 10 g/L |
| Yeast extract diafiltrate (1) | 10 g/L |
| $K_2HPO_4$ | 2.5 g/L |
| NaCl | 5.0 g/L |
| Glucose (2) | 5.0 g/L |
| Nicotinamide adenine dinucleotide (NAD) (3) | 2 mg/L |
| Hemin (4) | 5 mg/L |

The salts and soy peptone were dissolved in small volumes of hot, pyrogen-free water and brought to correct final volume with additional hot, pyrogen-free water. The fermenters or flasks were then sterilized by autoclaving for about 25 minutes at 121° C., and after cooling yeast extract diafiltrate (1), glucose (2), NAD (3), and hemin (4) were added aseptically to the flasks or fermenters prior to inoculation.

(1) Yeast extract diafiltrate: 100 g brewers' yeast extract (Amber) was dissolved in 1 liter distilled water and ultrafiltered using an Amicon DC-30 hollow fiber unit with H10×50 cartridges with a 50 kd cutoff. The filtrate was collected and sterilized by passage through a 0.22 μ filter.

(2) Glucose was prepared as a sterile 25% solution in distilled water.

(3) A stock solution of NAD containing 20 mg/mL was sterilized by passage through a (0.22 μ filter) and added aseptically just prior to inoculation.

(4) A stock solution of Hemin 3× was prepared by dissolving 200 mg in 10 mL of 0.1M NaOH and the volume adjusted with distilled, sterilized water to 100 mL. The solution was sterilized for 20 minutes at 121° C. and added aseptically to the final medium prior to inoculation.

C Stage: 70 Liter Seed Fermenter—Three liters of the product of B Stage was used to inoculate a fermenter containing about 40 liters of Complete Haemophilus Seed And Production medium (prepared as described above) and 17 mL UCON B625 antifoam agent. The pH at inoculation was 7.4.

D Stage: 800 Liter Production Fermenter—Approximately 40 liters of the product of "C Stage" was used to inoculate an 800 liter fermenter containing 570 liters of Haemophilus Seed and Production medium (prepared as described above), scaled to the necessary volume, and 72 mL of UCON LB625 antifoam agent was added.

The fermentation was maintained at 37° C. with 100 rpm agitation, with the $O.D._{660}$ and pH levels measured about every two hours until the $O.D._{660}$ was stable during a two-hour period, at which time the fermentation was terminated (a typical final $O.D._{660}$ was about 1.2 after about 20 hours).

HARVEST AND INACTIVATION

Approximately 600 liters of the batch was inactivated by harvesting into a "kill tank" containing 12 liters of 1% thimerosal.

CLARIFICATION

After 18 hours of inactivation at 4° C., the batch was centrifuged in a 4-inch bowl Sharples contiuous flow centrifuge at a flow rate adjusted to maintain product clarity (variable between 1.3 and 3.0 liters per minute). The supernatant obtained after centrifugation (15,000 rpm) was used for product recovery.

ISOLATION AND CONCENTRATION BY ULTRAFILTRATION

The supernatant from two production fermentations was pooled and concentrated at 2° to 8° C. in a Romicon XM-50 ultrafiltration unit with twenty 50 kd cut-off hollow fiber cartridges (4.5 m² membrane area; 2.0 Lpm air flow and 20 psi). Concentration was such that after approximately 4.5 hours, about 1,900 liters had been concentrated to 57.4 liters. The filtrate was discarded.

48% AND 61% ETHANOL PRECIPITATION

To the 57.4 liters of ultrafiltration retentate, 53 liters of 95% ethanol was added dropwise over 1 hour with stirring at 4° C. to a final concentration of 48% ethanol by volume. The mixture was stirred two additional hours at 4° C. to insure complete precipitation, and the supernatant was collected following passage through a single 4-inch Sharples continuous flow centrifuge at 15,000 rpm at a flow rate of about 0.4 liters per minute. The pellet was discarded and the clarified fluid was brought to 82% ethanol with the addition of 40.7 liters of 95% ethanol over a one hour period. The mixture was stirred for three additional hours to insure complete precipitation.

RECOVERY OF THE SECOND PELLET

The resulting 48% ethanol-soluble-82% ethanol-insoluble precipitate was collected by centrifugation in a 4 inch Sharples continuous flow centrifuge at 15,000 rpm with a flow rate of about 0.24 liters per minute and the 82% ethanol supernatant was discarded. The crude product yield was about 1.4 kg of wet paste.

CALCIUM CHLORIDE EXTRACTION

The 1.4 kg grams of 82% ethanol-insoluble material, was mixed in a Daymax dispersion vessel 2°–8° C. with 24.3 liters of cold, distilled water. To this mixture, 24.3 liters of cold 2M $CaCl_2.2H_2O$ was added, and the mixture was incubated at 4° C. for 15 minutes. The vessel was then rinsed with 2 liters of 1M $CaCl_2.2H_2O$, resulting in about 50 liters final volume.

23% ETHANOL PRECIPITATION

The 50 liters of $CaCl_2$ extract was brought to 25% ethanol by adding 16.7 liters of 95% ethanol dropwise, with stirring, at 4° C. over 30 minutes. After additional stirring for 17 hours, the mixture was collected by passage through a Sharples continuous flow centrifuge at 4° C. The supernatant was collected and the pellet was discarded.

38% ETHANOL PRECIPITATION AND COLLECTION OF CRUDE PRODUCT PASTE

The 25% ethanol-soluble supernatant was brought to 38% ethanol by the addition of 13.9 liters of 95% ethanol, dropwise with stirring, over a 30 minute period. The mixture was then allowed to stand with agitation for one hour, then without agitation for 14 hours, to insure complete precipitation. The resulting mixture was then centrifuged in a 4 inch Sharples continuous flow centrifuge at 15,000 rpm (flow rate of 0.2 liters per minute) to collect the precipitated crude *H. influenzae* polysaccharide.

TRITURATION

The pellet from the centrifugation was transferred to a 1 gallon Waring Blender containing 2 to 3 liters of absolute ethanol and blended for 30 seconds at the highest speed. Blending was continued for 30 seconds on, and 30 seconds off, until a hard white powder resulted. The powder was collected on a Buchner funnel with a teflon filter disc and washed sequentially, in situ, with two 1 liter portions of absolute ethanol and two 2 liter portions of acetone. The material was then dried, in vacuo, at 4° C. for 24 hours, resulting in about 337 g (dry weight) of product.

PHENOL EXTRACTION

About 168 grams of the dry material from the trituration step (about half of the total) was resuspended in 12 liters of 0.488M sodium acetate, pH 6.9, with the aid of a Daymax dispersion vessel. The sodium acetate solution was immediately extracted with 4.48 liters of a fresh aqueous phenol solution made as follows: 590 mL of 0.488M sodium acetate, pH 6.9, was added to each of eight 1.5 kg bottles of phenol (Mallinckrodt crystalline) in a 20 liter pressure vessel and mixed into suspension. Each phenol extract was centrifuged for 2.5 hours at 30,000 rpm and 4° C. in the K2 Ultracentrifuge (Electronucleonics). The aqueous effluent was extracted three additional times with fresh aqueous phenol solution as described above. The phenol phases were discarded.

ULTRAFILTRATION

The aqueous phase from the first phenol extraction above (12.2 liters) was diluted with 300 liters of cold, distilled water and diafiltered at 4° C. on an Amicon DC-30 ultrafiltration apparatus using 3 H10P10, 10 kd cutoff cartridges, to remove the carryover phenol. The Amicon unit was rinsed and the rinse added to the retentate, such that the final volume was 31.5 liters. The ultrafiltrate was discarded.

67% ETHANOL PRECIPITATION 0.81 liters of 2.0 M $CaCl_2$ was added to the 31.5 liters of dialysate from the previous step (final $CaCl_2$ concentration was 0.05M) and the solution was brought to 82% ethanol with dropwise addition and rapid stirring over one hour, of 48.5 liters of 95% ethanol. After 4 hours of agitation, then standing for 12 hours at 4° C., the supernatant was siphoned off and the precipitate was collected by centrifugation in a 4 inch Sharples continuous flow centrifuge (15,000 rpm), at 4° C. for 45 minutes. The resulting polysaccharide pellet was triturated in a 1 gallon Waring blender using 30 second pulses with 2 liters of absolute ethanol, collected on a Buchner funnel fitted with a teflon filter disc, and washed, in situ, with four 1 liter portions of absolute ethanol followed by two 1 liter portions of acetone. The sample was then dried in a tared dish, in vacuo, at 4° C. for 20 hours. The yield was about 102 grams of dry powder. The yield from all phenol extractions was pooled resulting in a total of 212.6 grams of dry powder.

ULTRACENTRIFUGATION IN 29% ETHANOL AND COLLECTION OF FINAL PRODUCT

The 212.6 grams of dry powder from above was dissolved in 82.9 liters of distilled water, to which was added 2.13 liters of 2M $CaCl_2.2H_2O$, (0.05M $CaCl_2$), 2.5 mg polysaccharide/mL), and the mixture was brought 29% ethanol with the dropwise addition of 29.86 liters of 95% ethanol over 30 minutes. The mixture was clarified immediately by centrifugation in a K2 Ultracentrifuge containing a K3 titanium bowl and a K11 Noryl core (30,000 rpm and 150 mL per minute flow rate) at 4° C. The pellet was discarded and the supernatant was brought to 38% ethanol by the addition of 17.22 liters of 95% ethanol over 30 minutes with stirring. After stirring 30 additional minutes the mixture was allowed too stand without agitation at 4° C. for 17 hours and the precipitate was collected using a 4 inch Sharples continuous flow centrifuge at 15,000 rpm (45 minutes was required).

The resulting paste was transferred to a 1-gallon Waring blender containing 2 liters of absolute ethanol and blended at the highest speed by 4 or 5 cycles of 30 seconds on, 30 seconds off, until a hard, white powder formed. This powder was collected on a Buchner funnel fitted with a Zitex teflon disc and rinsed sequentially, in situ, with two fresh 0.5 liter portions and one 1 liter portions of absolute ethanol, and with two 1 liter portion of acetone. The product was removed from the funnel and transferred to a tared dish for drying, in vacuo, at 4° C. (for 25 hours). The final yield of the product was 79.1 grams dry weight.

EXAMPLE 7

Culturing Streptococcus pneumoniae subtypes and Isolation of Crude Pn-Ps

I. Culturing Pneumococci

Methods of culturing pneumococci are well known in the art [Chase, M. W., *Methods of Immunology and Immunochemistry* 1, 52 (1967)]. Isolates of pneumococcal subtypes are available from the ATCC. The bacteria are identified as encapsulated, non-motile, Gram-positive, lancet-shaped diplococci that are alpha-hemolytic on blood-agar. Subtypes are differentiated on the basis of Quelling reaction using specific antisera. Master and stock seed cultures are preferably maintained lyophilized or below 8° C. In a preferred culture method, stock cultures are restored with Heart Infusion Broth, plated onto Heart Infusion Agar, containing 10% defibrinated rabbit blood, and incubated at 37° C.±2° C. for approximately 18 hours.

The growth on the plate is resuspended in Heart Infusion Broth and an aliquot of the resuspended growth is used to inoculate 100 ml of Heart Infusion Broth containg 10% defibrinated rabbit blood, which is incubated as a stationary culture for approximately 18 hours at 37° C.±2° C. The 100 ml of liquified culture (working seed) is checked for purity by microscopic examination of a Gram-stained smear and growth on Heart Infusion Blood Agar plates. The working seed may be stored at 2°-8° C. for up to 14 days or used immediately. Two-liter Erlenmeyer flasks or other suitable vessels, containing Pneumococcus Inoculum Medium (YUF), containing dextrose (25 gm/liter), are inoculated with working seed and incubated stationary for approximately 8-24 hours at 37° C.±2° C. The incubation period varies as specified depending on the type of Streptococcus pneumoniae being grown. The pH of the fermentation is adjusted to maintain a target pH range of 6.0 to 7.2 by the periodic addition of 12% sodium bicarbonate solution until an optical density of 1.5 to 4.0 is reached. Optical density is monitored at 660 nanometers. A sample of the growth is examined microscopically and a serological agglutination reaction is performed to check purity. The growth from this stage is transferred into a seed fermentor containing 40 liters of Pneumococcus Fermentor Medium composed of distilled water, a dry charge of the components for Pneumococcus seed medium (YUF), Yeast Extract Ultrafiltrate, UCON, and dextrose (approximately 25 gm/liter) The culture is incubated at 37° C.±2° C. with mild agitation for approximately 2-12 hours. The pH is controlled to 6.0 to 7.2 by the periodic addition of sodium hydroxide solution. A fermentor containing 525 liters of Pneumococcus Fermentor Medium, composed of distilled water, a dry charge of the components for Pneumococcus Production Medium YUF), Yeast Extract Ultrafiltrate, UCON, and dextrose (approximately 25 gm/liter), is inoculated with approximately 50 liters of one 2-12 hour seed culture, ? he culture is incubated at 37° C.±2° C. with mild agitation for 6-30 hours depending on which type is being grown. The pH is controlled at 6.0 to 7.2 by periodic additions of sodium hydroxide solution. The fermentation is followed by optical density determination, and the fermentation is terminated when the dextrose is completely utilized as indicated by no further changes in pH.

The pathogenic organisms are killed immediately after fermentation is terminated. This is accomplished by addition of phenol to a concentration of about 1% and the kill allowed to proceed for 2-12 hours at ambient temperature.

II) Isolating Crude Pn-Ps

Denatured alcohol is added to the killed culture in a sufficient quantity to precipitate cell debris and nucleic acids, which is removed by centrifugation. The crude polysaccharide is then precipitated from the supernatant by addition of more denatured ethanol. The solids are collected by centrifugation and the supernatant discarded.

Nucleic acid contamination is reduced by solubilization of the polysaccharide in a neutral aqueous solution such as 1-5% sodium acetate, or 0.05M phosphate buffer to which is added nuclease and about 0.01M magnesium chloride. After about 60-120 minutes at about 36° C., the pH is adjusted to about 8.0 and a protease such as trypsin, is added to digest proteinaceous contaminants.

Additional impurities may be eliminated by reprecipitation of the polysaccharide with sodium acetate and denatured alcohol or isoproanol followed by resolubilization in distilled water. Addition of cetrimonium bromide at about 8° C. precipitates impurities which are removed by centrifugation. Addition of sodium acetate and an alignat of denatured alcohol or isopropanol allows removal of additonal impurities. The polysaccharide is recovered by addition of more alcohol and centrifugation. The precipitate is washed with absolute ethanol until a white powder is obtained. The polysaccharide is collected by filtration, washed with absolute ethanol and acetone, and dried under vacuum to yield the crude Pn-Ps as a powder.

EXAMPLE 8

Preparation of Partially-Hydrolyzed, Purified Pn6B-Ps (1) Thermal Hydrolysis: A 3.0 g portion of crude Pn6B-Ps powder was solubilized in 1200 mL saline (0.9% NaCl) with stirring at room temperature for about 4 hours and stored at 4° C. overnight. The solution was then hydrolyzed in a cold-finger reflux condenser apparatus at 100° C. for 24 hours and cooled to room temperature. Sodium acetate reagent (59.7 g) was added to a final concentration of 3% (w/v).

(2) Serological Probe: An isopropanol (IPA) fractionation probe and antibody-directed end-point Nephelose assay, performed on a 10 mL portion of the sample, showed that the Pn6B-Ps would precipitate at 40-50% IPA.

(3) First IPA Addition: The hydrolyzed sample (volume—1210 mL, from step 1 above) was brought to 43.5% IPA by the addition of 932 mL IPA (added dropwise with stirring at room temperature). The sample was allowed to stir for 15-30 minutes and then centrifuged at 11,000×g for 30 minutes (Beckman JA-10 rotor; 8,000 rpm; 20° C.). The waste pellet was titrated with absolute EtOH in a 250-mL Omnimix jar, then collected on a 60-mL sinter glass funnel. The precipitate was washed directly on the funnel with absolute EtOH, then acetone, and dried in vacuo over $CaCl_2$ at room temperature in preparation for analysis.

(4) Second IPA Addition and Product Recovery: The 43.5% IPA supernatant fluid [volume =2020 mL, from step 3 above] was brought to 46.0% IPA by adding 93.5mL IPA dropwise while stirring at room temperature. The sample was aged and centrifuged as in step 3 above. The pellet was titrated, collected, washed and dried as in step 3 above. The Pn6B-Ps product weighed 1,650 mg.

(5) A total of 982 mg of Pn6B-Ps prepared as described above was mixed and solubilized in 393 mL $H_2O$ by stirring at room temperature for 2 hours. Sodium acetate reagent (19.6 g) was added to a final concentration of 4% (w/v). 590 mL IPA was added to the solution above (dropwise while stirring at room temperature) to a final concentration of 60%. The resulting precipitate was centrifuged, then titrated, collected, washed and dried as in (3). The dry weight of the processed Pn6B-Ps was 997 mg. It had a $K_D$ of 0.62 and a phosphorus content of 3.3%.

EXAMPLE 9

S. pneumoniae 6B-OMPC Conjugate Pn6B-Ps-OMPC

A. Preparation of Dowex 50×2 tetrabutylammonium Resin [Dowex 50 ($Bu_4N^\pm$)]

Dowex 50×2 (200–400 mesh) $H^+$ form, (72 g) was slurried in water, charged to a column, and washed sequentially with water, 6N HCl, and then water until the effluent tested neutral to pH paper. A 10% aqueous solution of tetrabutylammonium hydroxide was then run through the column until the effluent tested strongly alkaline. Finally, water was run through the column until the effluent again tested neutral.

B. Pn6B($Bu_4N+$):

Pn6B-Ps(600 mg), size reduced fractionated was dissolved in sterile distilled water (60 mL) and the solution magnetically stirred until all solids went into solution (1.5 h). The polysaccharide solution was applied to the rinsed resin and allowed to pass through the bed by gravity (4.5 h). The column was washed with water (10–12 mL) and the combined effluents lyophilized, providing 640 mg of dry Pn6B-Ps tetra-n-butyl ammonium salt, Pn6B(n-$Bu_4N+$).

C. Pn6B-$BuA_2$

Pn6B(n-$Bu_4N+$)(640 mg) was dissolved in dimethylsulfoxide (DMSO) (24 mL) and magnetically stirred for 30 min, at which time all solids appeared to be in solution. To this mixture was added 1, 1'-carbonyldiimidazole (44.2 mg), and the reaction stirred at room temperature (60 min). In a separate flask, a solution of butanediamine dihydrochloride ($BuA_2 \cdot 2HCl$, 1.022 g) in water (16 mL) was made basic (pH 10.2) by the addition of 10 N NaOH. The solution was filtered through a 0.2 μm sterile filter, and cooled in an ice bath. The aged DMSO mixture containing the activated polysaccharide was added to the cold $BuA_2$.2MCl solution, in a slow steady stream, and the resulting solution stirred at 0° C. (15 min). The reaction mixture was allowed to warm up to room temperature and stirred for an additional 1 h, after which it was transferred to dialysis tubing and dialyzed (4° C.) against the following: 1] 15 L of 0.1M pH 7.0 $NaPO_4$ buffer for 6 hr; 2] 15 L 0.01M pH 7.0 $NaPO_4$ buffer, 12 hr; 3] 15 L 0.01M pH 7.0 $NaPO_4$ buffer, 9 hr; 4] 15 L distilled $H_2O$, 17.5 hr. The contents of the dialysis tubing was lyophilized, providing 222 mg of Pn6B-1,4-butane diamine (Pn6B-$BuA_2$). The NMR (300 MHz, $D_2O$) of about 5 mg of this material revealed a loading of 22 diamine residues per 100 Pn6B-Ps repeating monomer units, by comparing the integrals of the resonances of the butane diamine methylenes and the rhamnose methyl protons of Pn6B-Ps.

Pn6B-$BuA_2$-BrAc

Pn6B-$BuA_2$ (210 mg) was dissolved in pH 9.04, 0.1M Kolthoff borate-phosphate buffer (21 mL) and the mixture magnetically stirred for 30 min to effect solution. To this aqueous solution was added a mixture consisting of p-nitrophenyl bromoacetate (210 mg) in acetonitrile (2.6 mL) and the reation stirred overnight (20 hr, 4° C.). The solution was transferred to dialysis tubing and dialyzed (4° C.) against the following: 1] 15 L sterile distilled $H_2O$, 12.3 hr; 2] 15 L sterile distilled $H_2O$, 8.25 hr; 3] 15 L sterile distilled water, 5.5 hr. From the contents of the bag, 1.7 ml was removed for assays (NMR and Viscotek) amd then 0.449 g of dried pH 8 phosphate buffer salt (prepared by lyophilising a 0.1M, pH 8 $NaPO_4$ solution) was added. After complete dissolution (30 min.), the solution was filtered through a sterile 0.2 μm filter, yielding a pH 8 solution of Pn6B-$BuA_2$-BrAc.

Pn6B-OMPC

Sterile OMPC (40 mL, 4.5 mg/ml) was pelleted by ultracentrifugation (4° C., 43 K rpm, 2 hr) in four 10 ml centrifuge tubes. Each pellet was resuspended in 3 mL of a sterile-filtered (0.22 μm sterile filtered) thiolation mixture which consisted of the following: N-acetylhomocysteine thiolactone hydrochloride (164 mg), ethylenediaminetetraacetic acid disodium salt (255 mg), and dithiothreitol (53 mg) in pH 11.09, $Na_2B_4O_7$ buffer (30 mL). The resuspended pellets were homogenized (Dounce), combined, the vessel degassed and blanketed with nitrogen, and aged overnight (19 hr) at room temperature. The solution was divided among three ultracentrifuge tubes topped with 1M $KH_2PO_4$, and the potein pelleted (4° C., 43 K rpm, 2 h). The pellets were resuspended in 0.1M $NaPO_4$, pH 8 buffer (30 mL), homogenized (Dounce) and repelleted (4° C., 43 K rpm, 2 h). The sterile protein pellet was used resuspended in the filtered 6B-$BuA_2$-BrAc solution. An Ellman's test was performed immediately, and showed an SH titer of 34 μmol. The reaction mixture was degassed, blanketed with nitrogen, and aged for 91 hr. at room temperature.

The Pn6B-OMPC conjugate produced in this manner may be reacted with a second polysaccharide activated so as to be reactive with the residual bromoacetyl moieties exhibited on the conjugated Pn6B. Thus, thiolated PnPs6A prepared according to Example 1, or thiolated PRP prepared according to Example 2, may be conjugated with the Pn6B-OMPC conjugate prepared in this Example to form an OMPC-heterodimeric conjugate.

What is claimed is:

1. A covalent protein-dimeric polysaccharide conjugate immunogen wherein:
   a first polysaccharide is covalently bound to a protein;
   a second polysaccharide is covalently bound to the first polysaccharide;
   the first and second polysaccharides are derived from one or two different species of pathogenic bacteria;
   the protein is the outer membrane protein complex derived from *Neisseria meningtidis* b, which enhances the immunogenicity of the polysaccharides to which it is covalently conjugated; and the polysaccharides are derived from the group of bacteria selected from *Haemophilus influenzae* b, *Streptococcus pneumoniae* subtype 1, 2, 3, 4, 5, 6 A, 6 B, 7 F, 8, 9 N, 9 V, 10 A, 11 A, 12 F, 14, 15 B, 17 F, 18 C, 19 A, 19 F, 20, 22 F, 23 F, 33 F.

2. A covalent heterodimeric polysaccharide-protein conjugate immunogen, having a general structure:
PS$_2$-spacer$_2$-PS$_1$-spacer$_1$-OMPC, wherein:
- OMPC the outer membrane protein complex of *Neisseria meningtidis* b, which is a protein moiety which acts as a carrier and confers enhanced immunogenicity on the polysaccharide moieties to which it is conjugated;
- PS$_1$ and PS$_2$ are the same or different bacterial polysaccharides; spacer$_1$ represents an atomic chain linking the PS$_1$ and OMPC moieties;
- spacer$_2$ represents an atomic chain linking the PS$_1$-spacer$_1$-OMPC complex to PS$_2$; and
- the polysaccharides are derived from the group of bacteria selected from *Haemophilus influenzae* b, *Streptococcus pneumoniae* subtype 1, 2, 3, 4, 5, 6 A, 6 B, 7 F, 8, 9 N, 9 V, 10 A, 11 A, 12 F, 14, 15 B, 17 F, 18 C, 19 A, 19 F, 20, 22 B, 23 F, 33 F.

3. The conjugate of claim 1 wherein the polysaccharides are derived from the group of bacteria selected from *Haemophilus influenzae* b, *Streptococcus pneumoniae* subtype 4, 6 B, 9 V, 14, 18 C, 19 F, and 23 F.

4. The conjugate of claim 2 wherein Ps$_1$ is polyribosyl ribitol phosphate, and Ps$_2$ is a capsular polysaccharide derived from *Streptococcus pneumoniae*.

5. The conjugate of claim 2 wherein Ps$_1$ is a capsular polysaccharide derived from *Streptococcus pneumoniae* and Ps$_2$ is polyribosyl ribitol phosphate.

6. A process for making a protein-heterodimeric polysaccharide conjugate immunogen which comprises either:
(I)
(a) solubilizing a first and a second polysaccharide preparation in separate containers in a non-hydroxylic organic solvent; (b) activating the solubilized polysaccharide preparations with a bifunctional reagent; (c) reacting the first activated polysaccharide preparation with a bis-nucleophile, (d) functionalizing the first modified polysaccharide by reacting it with a reagent generating electrophilic sites; (e) reacting a protein with a reagent generating nucleophilic groups; (f) reacting the first covalently-modified polysaccharide and the functionalized protein to form a stable covalently-bonded polysaccharide-protein conjugate; (g) purifying the conjugate to remove unreacted polysaccharides and proteins; (h) activating a second polysaccharide so as to be able to react with residual active sites on the first polysaccharide of the stable covalently-bonded conjugate; (i) reacting the stable polysaccharide-protein conjugate with the second polysaccharide; and (j) isolating the multivalent conjugate free of residual unreacted reagents; or,
(II)
(a) solubilizing a first and a second polysaccharide preparation in separate containers in a non-hydroxylic organic solvent; (b) activating the solubilized polysaccharide preparations with a bifunctional reagent; (c) reacting the first activated polysaccharide preparation with a bis-nucleophile, (d) functionalizing the first modified polysaccharide by reacting it with a reagent generating thiol groups; (e) reacting a protein with with a reagent generating electrophilic sites; (f) reacting the first covalently-modified polysaccharide and the functionalized protein to form a stable covalently-bonded polysaccharide-protein conjugate; (g) purifying the conjugate to remove unreacted polysaccharides and proteins; (h) activating a second polysaccharide so as to be able to react with residual active sites on the first polysaccharide of the stable covalently-bonded conjugate; (i) reacting the stable polysaccharide-protein conjugate with the second polysaccharide; and (j) isolating the multivalent conjugate free of residual unreacted reagents wherein said first and said second polysaccharide are derived from the group of bacteria selected from *Haemophilus influenzae* b, *Streptococcus pneumoniae* subtype 1, 2, 3, 4, 5, 6 A, 6 B, 7 F, 8, 9 N, 9 V, 10 A, 11 A, 12 F, 14, 15 B, 17 F, 18 C, 19 A, 19 F, 20, 22 F, 23 F, 33 F.

7. A process for making a protein-heterodimeric polysaccharide conjugate which comprises either:
(I)
a) forming a polysaccharide-protein conjugate having residual haloacetyl groups on the polysaccharide which are reactive toward sulfhydryl groups;
b) succinylating an amino derivatized second polysaccharide with S-acetylmercapto succinic anhydride and deacetylating with hydroxyl amine to form sulfhydryl groups such that this polysaccharide will react with the polysaccharide-protein conjugate displaying residual haloacetyl groups;
c) displacing the halogen from one of the residual haloacetyl groups on the polysaccharide-protein conjugate with the liberated sulfhydryl on the second polysaccharide; or
(II)
a) forming a polysaccharide-protein conjugate having residual sulfhydryl groups on the polysaccharide which are reactive toward a second haloacetylated polysaccharide;
b) haloacetylating a second polysaccharide such that this polysaccharide will react with the polysaccharide-protein conjugate displaying residual sulfhydryl groups;
c) displacing the halogen from the haloacetylated second polysaccharide with the sulfhydryl group displayed by the polysaccharide-protein conjugate wherein said first and said second polysaccharide are derived from the group of bacteria selected from *Haemophilus influenzae* b, *Streptococcus pneumoniae* subtype 1, 2, 3, 4, 5, 6 A, 6 B, 7 F, 8, 9 N, 9 V, 10 A, 11 A, 12 F, 14, 15 B, 17 F, 18 C, 19 A, 19 F, 20, 22 F, 23 F, 33 F.

* * * * *